US011213608B2

(12) United States Patent
Skardal et al.

(10) Patent No.: US 11,213,608 B2
(45) Date of Patent: Jan. 4, 2022

(54) COMPOSITIONS INCLUDING GELATIN NANOPARTICLES AND METHODS OF USE THEREOF

(71) Applicant: Wake Forest University Health Sciences, Winston-Salem, NC (US)

(72) Inventors: Aleksander Skardal, Clemmons, NC (US); Casey Cuvan Clark, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 182 days.

(21) Appl. No.: 16/533,326

(22) Filed: Aug. 6, 2019

(65) Prior Publication Data

US 2020/0108172 A1    Apr. 9, 2020

Related U.S. Application Data

(60) Provisional application No. 62/718,662, filed on Aug. 14, 2018.

(51) Int. Cl.
| | | |
|---|---|---|
| *A61K 9/50* | (2006.01) | |
| *A61L 27/22* | (2006.01) | |
| *A61L 27/24* | (2006.01) | |
| *A61L 27/38* | (2006.01) | |
| *A61L 27/52* | (2006.01) | |
| *B33Y 70/00* | (2020.01) | |
| *A61L 27/20* | (2006.01) | |
| *B33Y 10/00* | (2015.01) | |
| *B33Y 80/00* | (2015.01) | |

(52) U.S. Cl.
CPC ............ *A61L 27/222* (2013.01); *A61L 27/20* (2013.01); *A61L 27/24* (2013.01); *A61L 27/38* (2013.01); *A61L 27/52* (2013.01); *B33Y 70/00* (2014.12); *A61L 2400/06* (2013.01); *B33Y 10/00* (2014.12); *B33Y 80/00* (2014.12)

(58) Field of Classification Search
None
See application file for complete search history.

(56) References Cited

U.S. PATENT DOCUMENTS

| | | |
|---|---|---|
| 2011/0280914 A1 | 11/2011 | Prestwich et al. |
| 2012/0089238 A1 | 4/2012 | Kang et al. |
| 2012/0114670 A1 | 5/2012 | Land et al. |
| 2017/0107483 A1 | 4/2017 | Pendergraft et al. |
| 2017/0143831 A1 | 5/2017 | Varanasi et al. |
| 2017/0307598 A1 | 10/2017 | Skardal et al. |
| 2018/0000743 A1 | 1/2018 | Welker et al. |
| 2018/0008551 A1* | 1/2018 | Kannan ............... A61K 31/704 |
| 2018/0273904 A1 | 9/2018 | Skardal et al. |
| 2018/0291350 A1 | 10/2018 | Murphy et al. |
| 2018/0320141 A1 | 11/2018 | Atala et al. |
| 2018/0348203 A1 | 12/2018 | Skardal |
| 2019/0010288 A1* | 1/2019 | Lee ..................... A61L 27/3813 |
| 2019/0106673 A1* | 4/2019 | Skardal ................. A61L 27/50 |
| 2019/0345439 A1 | 11/2019 | Skardal et al. |
| 2020/0048601 A1 | 2/2020 | Skardal et al. |
| 2020/0179563 A1* | 6/2020 | Bagley ................... A61L 27/26 |

FOREIGN PATENT DOCUMENTS

| | | | |
|---|---|---|---|
| WO | WO-2010087912 A1 * | 8/2010 | ............ B22F 1/0096 |
| WO | 2017070698 | 4/2017 | |
| WO | 2018004906 | 1/2018 | |
| WO | 2018005964 | 1/2018 | |
| WO | 2018027023 | 2/2018 | |
| WO | 2018071354 | 4/2018 | |
| WO | 2018081425 | 5/2018 | |
| WO | 2019028131 | 2/2019 | |
| WO | 2019152767 | 8/2019 | |

OTHER PUBLICATIONS

"Gelatin nanoparticles by two step desolvation—a new preparation method, surface modifications and cell uptake", J. Microencapsulation, vol. 17, No. 2, 187-193 (Year: 2000).*
Bavli et al. "Real-time monitoring of metabolic function in liver-on-chip microdevices tracks the dynamics of mitochondrial dysfunction" Proceedings of the National Academy of Sciences, USA, 113(16):E2231-E2240 (2016).
Bertassoni et al. "Hydrogel Bioprinted Microchannel Networks for Vascularization of Tissue Engineering Constructs" Lab Chip, 14(13):2202-2211 (2014).
Billiet et al. "A review of trends and limitations in hydrogel-rapid prototyping for tissue engineering" Biomaterials, 33:6020-6041 (2012).
Boland et al. "Drop-on-demand printing of cells and materials for designer tissue constructs" Materials Science and Engineering: C, 27(3):372-376 (2007).
Chang et al. "Effects of Dispensing Pressure and Nozzle Diameter on Cell Survival from Solid Freeform Fabrication-Based Direct Cell Writing" Tissue Engineering Part A, 14(1):41-48 (2008).
Chimene et al. "Advanced Bioinks for 3D Printing: A Materials Science Perspective" Annals of Biomedical Engineering, 44(6):2090-2102 (2016).
Christensen et al. "Freeform inkjet printing of cellular structures with bifurcations" Biotechnology and Bioengineering, 112(5):1047-1055 (2015).
Coester et al. "Gelatin nanoparticles by two step desolvation—a new preparation method, surface modifications and cell uptake" Journal of Microencapsulation, 17(2):187-193 (2000).
Donderwinkel et al. "Bio-inks for 3D bioprinting; recent advances and future prospects" Polymer Chemistry, 8 (31):4451-4471 (2017).
Engler et al. "Matrix Elasticity Directs Stem Cell Lineage Specification" Cell, 126(4):677-689 (2006).
Gao et al. "Coaxial nozzle-assisted 3D bioprinting with built-in microchannels for nutrients delivery" Biomaterials, 61:203-215 (2015).

(Continued)

*Primary Examiner* — Susan T Tran
(74) *Attorney, Agent, or Firm* — Myers Bigel, P.A.

(57) ABSTRACT

Described herein are gelatin nanoparticles including their use in a composition. The composition may comprise a plurality of gelatin nanoparticles, at least one polymer, and water. In some embodiments, the composition comprises cells. The composition may be in the form of a hydrogel. Methods of using such gelatin nanoparticles and/or compositions are also described.

15 Claims, 8 Drawing Sheets

(56) References Cited

OTHER PUBLICATIONS

Hewitt et al. "Phase I and II enzyme characterization of two sources of HepG2 cell lines" Xenobiotica, 34(3):243-256 (2004).
Hinton et al. "Three-dimensional printing of complex biological structures by freeform reversible embedding of suspended hydrogels" Science Advances, 1(9):e1500758 (2015).
Ingber, Donald E. "Cellular mechanotransduction: putting all the pieces together again" The FASEB Journal, 20:811-827 (2006).
Insphero AG "3D InSightTM Human Liver Microtissues" Brochure (2 pages) (2012).
Isaacson et al. "3D bioprinting of a corneal stroma equivalent" Experimental Eye Research, 173:188-193 (2018).
Jang et al. "3D printed complex tissue construct using stem cell-laden decellularized extracellular matrix bioinks for cardiac repair" Biomaterials, 112:264-274 (2017).
Kolesky et al. "3D Bioprinting of Vascularized, Heterogeneous Cell-Laden Tissue Constructs" Advanced Materials, 26(19):3124-3130 (2014).
Lopez-Barneo et al. "Chemotransduction in the carotid body: K+ current modulated by PO2 in type I chemoreceptor cells" Science, 241(4865):580-582 (1988).
Markstedt et al. "3D Bioprinting Human Chondrocytes with Nanocellulose-Alginate Bioink for Cartilage Tissue Engineering Applications" Biomacromolecules, 16(5):1489-1496 (2015).
Mazzocchi et al. "Optimization of collagen type I-hyaluronan hybrid bioink for 3D bioprinted liver microenvironments" Biofabrication, 11(1):015003 (2018).
Mewis et al. "Thixotropy" Advances in Colloid and Interface Science, 147-148:214-227 (2009).
Miller et al. "Rapid casting of patterned vascular networks for perfusable engineered three-dimensional tissues" Nature Materials, 11(9):768-774 (2012).
Montoro et al. "Oxygen Sensing by Ion Channels and Chemotransduction in Single Glomus Cells" The Journal of General Physiology, 107(1):133-143 (1996).
Murphy et al. "3D bioprinting of tissues and organs" Nature Biotechnology, 32(8):773-785 (2014).
Nair et al. "Characterization of cell viability during bioprinting processes" Biotechnology Journal, 4(8):1168-1177 (2009).
Owens et al. "Biofabrication and testing of a fully cellular nerve graft" Biofabrication, 5(4):045007 (2013).
Park et al. "Advances in three-dimensional bioprinting for hard tissue engineering" Tissue Engineering and Regenerative Medicine, 13(6):622-635 (2016).
Pati et al. "Printing three-dimensional tissue analogues with decellularized extracellular matrix bioink" Nature Communications, 5(3935):1-11 (2014).
Peng et al. "Bioprinting towards Physiologically Relevant Tissue Models for Pharmaceutics" Trends in Biotechnology, 34(9):722-732 (2016).
Prestwich et al. "Simplifying the Extracellular Matrix for 3-D Cell Culture and Tissue Engineering: A Pragmatic Approach" Journal of Cellular Biochemistry, 101:1370-1383 (2007).
Ramaiahgari et al. "A 3D in vitro model of differentiated HepG2 cell spheroids with improved liver-like properties for repeated dose high-throughput toxicity studies" Archives of Toxicology, 88(5):1083-1095 (2014).
Rodriguez-Antona et al. "Cytochrome P450 expression in human hepatocytes and hepatoma cell lines: molecular mechanisms that determine lower expression in cultured cells" Xenobiotica, 32(6):505-520 (2002).
Schuurman et al. "Gelatin-Methacrylamide Hydrogels as Potential Biomaterials for Fabrication of Tissue-Engineered Cartilage Constructs" Macromolecular Bioscience, 13(5):551-561 (2013).
Skardal et al. "Perspective: 'Universal' bioink technology for advancing extrusion bioprinting-based biomanufacturing" Bioprinting, 10:e00026 (2018).
Smith et al. "Three-Dimensional BioAssembly Tool for Generating Viable Tissue-Engineered Constructs" Tissue Engineering, 10(9/10):1566-1576 (2004).
Suntornnond et al. "A highly printable and biocompatible hydrogel composite for direct printing of soft and perfusable vasculature-like structures" Scientific Reports, 7(16902):1-11 (2017).
Wang, Ning "Review of Cellular Mechanotransduction" Journal of Physics D: Applied Physics, 50(23):1-14 (2017).
Wells, Rebecca G. "The role of matrix stiffness in regulating cell behavior" Hepatology, 47(4):1394-1400 (2008).
Wilkening et al. "Comparison of primary human hepatocytes and hepatoma cell line Hepg2 with regard to their biotransformation properties" Drug Metabolism and Disposition: The Biological Fate of Chemicals, 31(8):1035-1042 (2003).
Zhao et al. "In vitro vascularization of a combined system based on a 3D printing technique" Journal of Tissue Engineering and Regenerative Medicine, 10(10):833-842 (2016).

* cited by examiner

COMPOSITIONS INCLUDING GELATIN NANOPARTICLES AND METHODS OF USE THEREOF

RELATED APPLICATION DATA

This application claims the benefit of and priority to U.S. Provisional Application No. 62/718,662 filed Aug. 14, 2018, which is incorporated herein by reference in its entirety.

GOVERNMENT SUPPORT

This invention was made with government support under U. S. Army Medical Research and Materiel Command (USAMRMC) prototype Other Transaction Agreement W81XWH-15-9-0001, awarded to Advanced Technology International (ATI) as the Consortium Manager of the Medical Technology Enterprise Consortium (MTEC). The U.S. Government has certain rights in the invention.

FIELD

The present invention generally relates to compositions comprising gelatin nanoparticles and methods of using such compositions.

BACKGROUND

Bioprinting has become a staple of regenerative medicine and tissue engineering. It allows for three-dimensional (3D) tissue constructs to be fabricated on demand in a variety of shapes and sizes with many combinations of cells. These constructs can be used for novel in vitro models of diseases and therapies which can more accurately represent the in vivo pathology. While these 3D constructs mimic the in vivo environment and response better than two-dimensional (2D) cultures, they are not yet at a sufficient level of complexity that accurately represents physiological structures. For this next hurdle to be met, the materials for bioprinting, called bioinks, need to be improved.

Different types of bioprinting may have different requirements and/or materials. Stereolithography (SLA) techniques need a less viscous, light curable bioink to act as a resin. Drop-by-drop (DbD) techniques, such as laser induced forward transfer and inkjet, need low viscosity materials with high surface tension to accurately form consistent drops. The most common and versatile method of bioprinting is extrusion, based bioprinting, which, unlike the others, can work with a variety of materials and place down multiple types of distinct bioinks. The current level of technology limits the SLA and DbD techniques to using one material. Commercially available desktop bioprinters can have up to five or more different syringes, and thus different bioinks, to produce constructs. While the precision of extrusion based bioprinters is not as fine as SLA or DbD techniques, its ability to use multiple bioinks, the range of bioinks available for printing, the volume of the constructs it can print, and the cost of the printer make extrusion based bioprinting the most popular method for current research.

The main disadvantage of extrusion bioprinters is the material that they use to print. Bioinks are commonly made of hydrogels, either synthetic or naturally derived, which have poor mechanical properties. Unless specialized processing methods are employed, there is no easy way to accurately place hydrogel bioinks or stack multiple layers of hydrogel bioinks to produce significant features in the third dimension while keeping the printing conditions simple, e.g. room temperature and high water content. The bioprinters themselves are capable of great accuracy, on the order of 50 microns or less, but the loss moduli of hydrogel bioinks at room temperature prevents high definition printing. Creating a bioink capable of supporting itself under standard environmental conditions would greatly improve the capabilities of extrusion bioprinting.

SUMMARY

Aspects of the present invention relate to gelatin nanoparticles and use thereof. One aspect of the present invention is directed to gelatin nanoparticles having a diameter, on average, of about 150, 200, 250, or 300 nm to about 350, 400, 450, or 500 nm. In some embodiments, the gelatin nanoparticles are crosslinked, optionally wherein the gelatin nanoparticles are crosslinked with glutaraldehyde.

Another aspect of the present invention is directed to compositions comprising gelatin nanoparticles. The compositions can comprise gelatin nanoparticles, at least one polymer, and water. In some embodiments, the gelatin nanoparticles are present in the composition in an amount of about 10, 20, 30, 40, 50, 60, 70, 80, 90, 100, 120, 130, 140, or 150 to about 160, 170, 180, 190, 200, 210, 220, 230, 240, or 250 mg/mL.

A further aspect of the present invention is directed to a method of making a three-dimensional construct, the method comprising depositing a composition of the present invention (e.g., one including gelatin nanoparticles) onto a substrate and/or into a composition, thereby forming the three-dimensional construct. In some embodiments, the composition of the present invention is deposited by extrusion through a syringe and/or needle. In some embodiments, a composition comprising gelatin nanoparticles as described herein is a suspension (e.g., a homogeneous suspension).

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
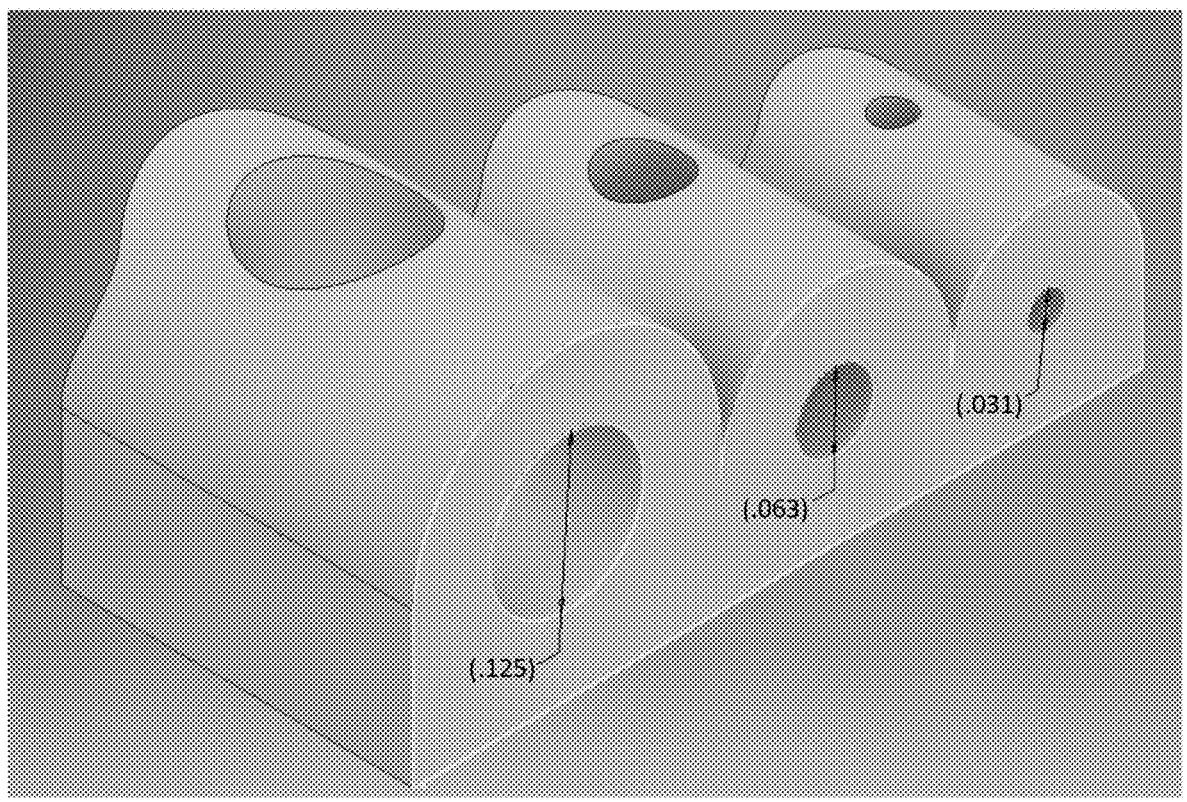
FIG. 1 shows the geometry for a test construct with the dimensions shown in inches.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Cells" and "cell" as used in the present invention are, in general, animal cells, particularly mammalian and/or primate cells, examples of which include, but are not limited to human, dog, cat, rabbit, monkey, chimpanzee, cow, pig, and goat. The cells may be differentiated at least in part to a particular cell or tissue type, such as liver, intestine, pancreas, lymph node, smooth muscle, skeletal muscle, cardiac muscle, central nerve, peripheral nerve, skin, bone, lung, breast, testes, immune system, etc. In some embodiments, the cells are diseased cells, optionally cancer cells. In some embodiments, a cell may express (naturally or by recombinant techniques) a detectable compound, which is a compound that provides and/or generates a detectable signal that allows for differentiation and/or identification of a cell and/or cell population such as, e.g., a fluorescent compound. In some embodiments, cells may be obtained from a subject, such as, for example, a subject or patient undergoing treatment for cancer. In some embodiments, a tissue biopsied from a subject may be used to prepare one or more organoids of the present invention, optionally with cells obtained from a 2 mm×2 mm minced tissue.

Cells (e.g., live cells) may be incorporated into a composition and/or hydrogel of the present invention in any suitable form, including as unencapsulated cells, or as cells previously aggregated as spheroids, or pre-formed organoids. Animal tissue cells aggregated or contained in cell spheroids can be produced in accordance with known techniques, or in some cases are commercially available (see, e.g., Insphero A G, 3D Hepg2 Liver Microtissue Spheroids (2012); Inspherio A G, 3D InSight™ Human Liver Microtissues, (2012)).

"Three-dimensional tissue construct" as used herein refers to a plurality of live cells, optionally in a carrier media, that are arranged in a three-dimensional or multi-layered configuration (as opposed to a monolayer). An "organoid" as used herein refers to a composition of live cells, typically in a carrier media, arranged in a three-dimensional or multi-layered configuration (as opposed to a monolayer) and is a type of three-dimensional tissue construct.

In some embodiments, an organoid may be referred to as a three-dimensional tissue construct. Alternatively, in some embodiments, a three-dimensional tissue construct refers to a construct that is a larger than an organoid such as, e.g., a structure that resembles an organ or tissue in a subject or a portion thereof. A three-dimensional tissue construct (e.g., an organoid) is an artificial, three-dimensional construct created in vitro to mimic or resemble the functionality and/or histological structure of an organ, tissue, or a portion thereof. Suitable carrier media for a three-dimensional tissue construct (e.g., an organoid) include hydrogels, such as cross-linked hydrogels as described below. In some embodiments, a three-dimensional tissue construct (e.g., an organoid) is formed upon cross-linking (e.g., after UV initiated cross-linking) of the carrier media (e.g., hydrogel). Additional example hydrogels include, but are not limited to, those described in PCT/US2015/055699, PCT/US2016/054607, and PCT/US2017/058531, the contents of each of which are incorporated herein by reference in their entirety. A three-dimensional tissue construct may comprise one or more (e.g., 1, 2, 3, 4, or more) differentiated cell type(s) depending upon the particular tissue and/or organ being modeled or emulated. Some three-dimensional tissue constructs may comprise diseased cells and/or cancer cells. When the three-dimensional tissue construct comprises diseased cells and/or cancer cells, they may include tissue cells and/or may include a tissue mimic without cells, such as an extracellular matrix (or proteins and/or polymers derived therefrom), hyaluronic acid, gelatin, collagen, alginate, etc., including combinations thereof. Thus, in some embodiments, cells are mixed together with an extracellular matrix, or cross-linked matrix, to form a three-dimensional tissue construct.

In some embodiments, a three-dimensional tissue construct (e.g., organoid) may be present in and/or formed in a hydrogel comprising thiolated hyaluronic acid (also referred to interchangeably herein as thiol-modified hyaluronic acid), methacrylated collagen (also referred to interchangeably herein as methacrylate-modified collagen), and water.

In some embodiments, a three-dimensional tissue construct (e.g., organoid) of the present invention comprises cells that are human-derived cells, and, in some embodiments, the cells consist of human-derived cells. A three-dimensional tissue construct (e.g., organoid) of the present invention may express and/or produce one or more biomarkers (e.g., 1, 2, 3, 4, or more) that are the same as a biomarker produced by the cells in vivo. For example, liver cells in vivo produce albumin and a three-dimensional tissue construct of the present invention comprising liver cells may express albumin. In some embodiments, a three-dimensional tissue construct may express a biomarker in the same amount or in an amount that is ±20%, ±10%, or ±5% of the average amount produced and/or expressed by corresponding cells in vivo. Example biomarkers include, but are not limited to, albumin, urea, glutathione S-transferase (GST) (e.g., α-GST), chemokines (e.g., IL-8, IL-1β, etc.), prostacyclin, SB100B, neuron-specific enolase (NSE), myelin basic protein (MBP), hormones (e.g., testosterone, estradiol, progesterone, etc.), inhibin A/B, lactate dehydrogenase (LDH), and/or tumor necrosis factor (TNF). The cells may be differentiated or undifferentiated cells, but are, in some embodiments, tissue cells (e.g., liver cells such as hepatocytes, pancreatic cells, cardiac muscle cells, skeletal muscle cells, etc.).

In some embodiments, a three-dimensional tissue construct of the present invention is not prepared from and/or does not comprise cells from an immortalized cell line. A three-dimensional tissue construct of the present invention may comprise and/or be prepared using high functioning cells, such as, but not limited to, primary cells and/or stem cells, e.g., induced pluripotent stems and/or differentiated iPS-derived cells.

In some embodiments, one or more populations of cells (optionally labeled with a detectable compound) may be added to a composition of the present invention. In some embodiments, the one or more populations of cells may be used to form a three-dimensional tissue construct (e.g., an organoid) as described herein that is encapsulated by a composition (e.g., hydrogel) of the present invention. One or more different populations of cells in a three-dimensional tissue construct of the present invention may be present in substantially the same (e.g., within about ±20%) amount as the amount of cells in that population in a tissue and/or tumor in vivo. In some embodiments, when cells have been obtained from a tissue sample from a subject, sorted and/or labeled, the different populations of cells are combined in substantially the amount as the amount present in the tissue sample.

In some embodiments, an organoid is about 100 μm or 200 μm to about 350 or 500 μm in diameter in at least one dimension, such as, for example, about 100, 150, 200, 250, 300, 350, 400, 450, or 500 μm in at least one dimension. In some embodiments, an organoid is about 1 μL to about 20 μL in volume such as, for example, about 1, 2, 3, 4, 5, 6, 7, 8, 9, 10, 11, 12, 13, 14, 15, 16, 17, 18, 19, or 20 μL in volume. The organoid may comprise about 1,500, 2,000, or 5,000 to about 10,000, 25,000, or 50,000 cells in total or about 1,000, 5,000, 10,000, or 50,000 to about 75,000, 100,000, 150,000, 250,000, 500,000, 750,000, 1,000,000, 50,000,000, or 100,000,000 cells in total. In some embodiments, an organoid of the present invention may comprise about 1, 2, or 5 million to about 10, 50, or 100 million cells per mL. In some embodiments, an organoid of the present invention may comprise about 10 million cells per mL. An organoid of the present invention may be in any suitable shape, such as, e.g., any three-dimensional shape and/or multi-layered shape. In some embodiments, an organoid of the present invention is in the form of a spheroid. In some embodiments, an organoid of the present invention may be self-organized in a composition of the present invention (e.g., a cross-linked hydrogel).

"Growth media" and "cell culture media" are used interchangeably herein and may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof. In some embodiments, the growth media includes a pH color indicator (e.g., phenol red).

A composition of the present invention may be used to prepare a three-dimensional tissue construct (e.g., organoid). In some embodiments, a composition of the present invention may be referred to as a "bioink" or a "bioink composition" (both of which are used interchangeably herein), and may comprise one or more live cell(s). However, the compositions of the present invention are not limited to use as a bioink and/or in bioprinting and may be useful in other areas, such as, for example, for encapsulation and/or delivery of an agent. In some embodiments, a composition of the present invention is a suspension (e.g., a homogeneous suspension), optionally wherein gelatin nanoparticles are suspended in a carrier media (e.g., hydrogel) or bioink that optionally comprises a plurality of cells. In some embodiments, at least a portion of gelatin nanoparticles present in a composition of the present invention are not dissolved in the composition. In some embodiments, more than 90% or all of gelatin nanoparticles present in a composition of the present invention are not dissolved in the composition. A composition of the present invention may provide a self-supporting structure and the composition may be devoid of a sacrificial support material.

Choice of cells will depend upon the particular three-dimensional tissue construct being created. For example, for a liver organoid, liver hepatocyte cells may be used. For a peripheral or central nerve organoid, peripheral nerve cells, central nerve cells, glia cells, or combinations thereof may be used. For a bone organoid, bone osteoblast cells, bone osteoclast cells, or combinations thereof may be used. For a lung organoid, lung airway epithelial cells may be used. The cells may be differentiated upon initial incorporation into the composition, or undifferentiated cells that are subsequently differentiated may be used. Additional cells may be added to any of the compositions and/or hydrogels.

According to some embodiments of the present invention provided are gelatin nanoparticles. Gelatin nanoparticles of the present invention may have, on average, a diameter of about 150, 200, 250, or 300 nm to about 350, 400, 450, or 500 nm. In some embodiments, a gelatin nanoparticle of the present invention has, on average, a diameter of about 150, 175, 200, 225, 250, 275, 300, 325, 350, 375, 400, 425, 450, 475 or 500 nm.

Gelatin nanoparticles of the present invention may have a zeta potential of about +15 mV to about +25 mV, optionally as measured using dynamic light scattering. In some embodiments, the gelatin nanoparticles have a zeta potential of about +15, +16, +17, +18, +19, +20, +21, +22, +23, +24, or +25 mV. In some embodiments, the gelatin nanoparticles have a zeta potential of about +20 mV.

Gelatin nanoparticles of the present invention may have, on average, a molecular weight of about 10, 50, 100, 250, or 500 kDa to about 750, 1000, 1250, 1500, or 2000 kDa. In some embodiments, a gelatin nanoparticle of the present invention has, on average, a molecular weight of about 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 kDa.

In some embodiments, gelatin nanoparticles of the present invention may aggregate to each other when present in a composition (e.g., an aqueous composition, a hydrogel, a bioink, etc.). Aggregation of the gelatin nanoparticles may occur via one or more interaction(s) such as, but not limited to, hydrogen bonding (e.g., reversible hydrogen bonding), electrostatic, and/or non-covalent interactions (e.g., peptide-peptide non-covalent interactions). In some embodiments, aggregates of gelatin nanoparticles may have, on average, a diameter of about 1, 1.5, 2, 2.5, 3, 3.5, 4, 4.5, or 5 µm to about 5.5, 6, 6.5, 7, 7.5, 8, 8.5, or 9 µm. In some embodiments, aggregates of gelatin nanoparticles may have, on average, a diameter of about 5 µm. In some embodiments, gelatin nanoparticles may be added to a composition in the form of aggregates, and the aggregates may break apart upon addition to the composition. Aggregates of gelatin nanoparticles may be suspended in a carrier media (e.g., hydrogel) or bioink that optionally comprises a plurality of cells. Aggregates of gelatin nanoparticles may not be dissolved in a composition of the present invention.

In some embodiments, a gelatin nanoparticle of the present invention comprises one or more functional group(s) that are available to interact with one or more functional group(s) of another gelatin nanoparticle and/or another component present in a composition in which the gelatin nanoparticles and component are present. Exemplary functional groups include, but are not limited to, those that provide hydrogen bonding (e.g., reversible hydrogen bonding), an amine, an alkynyl imine, an alkynyl amine, an alkenyl imine, alkenyl amine, an acrylate imine, an acrylate amine, a methacrylate imine, a maleimide, an acrylate, a methacrylate, a thiol, a carboxyl, alkyne, and/or a methacrylate amine. In some embodiments, the one or more functional group(s) of the gelatin nanoparticle, that are available to interact with another gelatin nanoparticle and/or component, are present on the surface of the gelatin nanoparticle. In some embodiments, the one or more functional group(s) increase the amount and/or strength of aggregation between the gelatin nanoparticles and/or improve the thixotropic character of a composition in which the gelatin nanoparticles are present.

In some embodiments, a gelatin nanoparticle of the present invention is crosslinked. In some embodiments, gelatin nanoparticle of the present invention is crosslinked with a crosslinking agent such as, but not limited to, glutaraldehyde.

Gelatin nanoparticles of the present invention may be prepared using methods known to those of skill in the art. For example, in some embodiments, a gelatin nanoparticle is prepared using one or more steps described in Coester, C. J., et al., *J. Microencapsulation,* 2000, Vol. 17, No. 2, 187-193, the contents of which are incorporated herein by reference in their entirety. In some embodiments, gelatin nanoparticles of the present invention are prepared using methods described herein.

In some embodiments, a method of the present invention may comprise preparing a gelatin nanoparticle of the present invention and may optionally include a step of crosslinking the gelatin nanoparticle and/or adding one or more functional group(s) to the gelatin nanoparticle. Crosslinking may be carried out and/or accomplished by reacting a crosslinking agent (e.g., glutaraldehyde) with the gelatin nanoparticles. In some embodiments, adding one or more functional group(s) to the gelatin nanoparticle includes reacting a catechol amine, a catechol containing an alkynyl imine, a catechol containing an alkynyl amine, a catechol containing an alkenyl imine, a catechol containing an alkenyl amine, a catechol containing an acrylate imine, a catechol containing an acrylate amine, a catechol containing a methacrylate imine, a maleimide, and/or a catechol containing a methacrylate amine with the gelatin nanoparticles. In some embodiments, a gelatin nanoparticle may be reacted with a small molecule compound as described in U.S. Provisional Application Ser. No. 62/570,825 filed Oct. 11, 2017 and/or PCT/US2017/058531, the contents of each of which are incorporated herein by reference in their entirety. In some embodiments, the functional group added to the gelatin nanoparticles is a functional group that provides hydrogen bonding (e.g., reversible hydrogen bonding) and/or is an amine, an alkynyl imine, an alkynyl amine, an alkenyl imine, alkenyl amine, an acrylate imine, an acrylate amine, a methacrylate imine, a maleimide, an acrylate, a methacrylate, a thiol, a carboxyl, alkyne, and/or a methacrylate amine.

In some embodiments, a method of preparing a gelatin nanoparticle of the present invention comprises milling and/or grinding (e.g., cryomilling) gelatin nanoparticles to a given size and/or to powderize the nanoparticles.

Gelatin nanoparticles of the present invention may be used in a composition (e.g., an aqueous composition, a hydrogel, a bioink, etc.) to modify one or more properties of the composition (e.g., thixotrophy, stiffness, etc.) and/or to add one or more functionalities to the composition (e.g., additional crosslinking and/or binding sites, etc.).

In some embodiments, a composition of the present invention comprises gelatin nanoparticles of the present invention and at least one polymer. Exemplary polymers include, but are not limited to proteins (e.g., collagen, gelatin, etc.), peptides, polysaccharides (e.g., celluloses, chitosan, alginates, etc.), polymers that can be crosslinked with itself, polymers that can be crosslinked with another component (e.g., in the presence of a crosslinking agent), thermo-responsive polymers, hyaluronates (e.g., hyaluronic acid), biocompatible polymers, natural polymers (e.g., silk), synthetic polymers (e.g., poly(acrylic acid) and derivatives thereof, poly(ethylene oxide) (PEG) and copolymers and/or derivatives thereof (e.g., PEG derivatives include, but are not limited to, poly(ethylene glycol) diacrylate (PEGDA) and PEG-di-maleimide), poly(vinyl alcohol), polyphosphazene, poloxamer, hydroxyethyl methacrylate, polydimethylsiloxane, polyacrylamide, poly(lactic acid), etc.), and/or biodegradable polymers. In some embodiments, the composition is an aqueous composition, optionally a hydrogel. In some embodiments, the composition is a composition such as, but are not limited to, one described in PCT/US2015/055699, PCT/US2016/054607, and PCT/US2017/058531, the contents of each of which are incorporated herein by reference in their entirety. In some embodiments, the composition comprises gelatin nanoparticles of the present invention, thiolated hyaluronic acid, methacrylated collagen (e.g., methacrylated Type 1 collagen), and water. In some embodiments, the composition is a composition such as, but are not limited to, one described in U.S. Provisional Application Ser. No. 62/570,825 filed Oct. 11, 2017, the contents of which are incorporated herein by reference in their entirety.

Gelatin nanoparticles may be present in a composition of the present invention in an amount of about 10, 20, 30, 40, 50, 60, 70, 80, 90, 100, 110, 120, 130, 140, or 150 to about 160, 170, 180, 190, 200, 210, 220, 230, 240, or 250 mg/mL. In some embodiments, gelatin nanoparticles may be present in a composition of the present invention in an amount of about 10, 20, 30, 40, 50, 60, 70, 80, 90, 100, 110, 120, 130, 140, 150, 160, 170, 180, 190, 200, 210, 220, 230, 240, or 250 mg/mL.

In some embodiments, a composition of the present invention comprises gelatin, that is not in the form of nanoparticles, in an amount of about 1, 5, 10, 15, 20, 25, 30, 35, or 40 mg/mL to about 45, 50, 55, 60, 65, 70, or 75 mg/mL. In some embodiments, gelatin, that is not in the form of nanoparticles, may be present in a composition of the present invention in an amount of about 1, 5, 10, 15, 20, 25, 30, 35, 40, 45, 50, 55, 60, 65, 70, or 75 mg/mL.

In some embodiments, a composition of the present invention comprises methacrylated collagen in an amount of about 0.5 mg/mL of the composition to about 10 mg/mL of the composition. In some embodiments, the composition comprises methacrylated collagen in an amount of about 1, 2, 3, 4, 5, or 6 mg/mL of the composition or about 7, 8, 9, 10, 11, or 12 mg/mL of the composition. In some embodiments, the composition comprises methacrylated collagen in an amount of about 1, 2, 3, 4, 5, 6, 7, 8, 9, 10, 11, or 12 mg/mL of the composition. In some embodiments, methacrylated collagen is as described in U.S. Provisional Application Ser. No. 62/570,825 filed Oct. 11, 2017, the contents of which are incorporated herein by reference in their entirety.

In some embodiments, a composition of the present invention comprises thiolated hyaluronic acid in an amount of about 0.1% to about 2% w/v of the composition. In some embodiments, a composition of the present invention comprises thiolated hyaluronic acid in an amount of about 0.1% to about 2% w/v of the composition. In some embodiments, thiolated hyaluronic acid is as described in U.S. Provisional Application Ser. No. 62/570,825 filed Oct. 11, 2017, the contents of which are incorporated herein by reference in their entirety.

In some embodiments, the composition has a ratio of thiolated hyaluronic acid to methacrylated collagen in a range from 1:0.5 to 1:10 (thiolated hyaluronic acid:methacrylated collagen) by volume. In some embodiments, the ratio by volume of the thiolated hyaluronic acid to the methacrylated collagen is about 1:0.5, 1:1, 1:2, 1:3, 1:4, 1:5, 1:6, 1:7, 1:8, 1:9, or 1:10. In some embodiments, a composition of the present invention comprises a greater number of methacrylate groups (e.g., from the methacrylated collagen) than the number of thiols (e.g., from the thiolated hyaluronic acid). The number of methacrylate group may be about 2, 3, 4, 5, 6, 7, 8, 9, or more times greater than the number of thiols.

A composition of the present invention may include an initiator (e.g., a thermal or photoinitiator). Any suitable initiator that catalyzes the reaction of a polymer and/or gelatin nanoparticle present in the composition may be employed. For example, in some embodiments, the initiator catalyzes a reaction between unreacted methacrylate groups (e.g., unreacted metacrylate groups on the methacrylated collagen) present in the composition. Example photoinitiators include, but are not limited to, 4-(2-hydroxyethoxy) phenyl-(2-hydroxy-2-propyl)ketone, 2-hydroxy-4'-(2-hydroxyethoxy)-2-methylpropiophenone, and/or IRGACURE® commercially available from BASF. In some embodiments, an initiator (e.g., a photoinitiator) may be present in a composition of the present invention in an amount from about 0.01% to about 0.1% or 1% w/v of the composition. In some embodiments, the initiator is present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v of the composition.

Water may be present in a composition of the present invention in any suitable amount. In some embodiments, water may be present in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the composition. In some embodiments, the composition is in the form of a hydrogel, optionally an extrudable hydrogel.

Cells (e.g., live cells) may be present in a composition of the present invention in any suitable amount. In some embodiments, the concentration of cells present in a composition may depend on the size of a desired three-dimensional tissue construct to be prepared from the composition and/or the number of three-dimensional tissue constructs to be prepared from the composition. In some embodiments, a composition of the present invention comprises about 1,500, 2,000, or 5,000 to about 10,000, 25,000, or 50,000 cells in total or about 1,000, 5,000, 10,000, or 50,000 to about 75,000, 100,000, 150,000, 250,000, 500,000, 750,000, 1,000,000, 50,000,000, or 100,000,000 cells in total. In some embodiments, a composition of the present invention may comprise about 1, 2, or 5 million to about 10, 50, 100, 250, or 500 million cells per mL.

One or more (e.g., 1, 2, 3, 4, 5, 6, 7, or more) additional components may be present in a composition of the present invention. For example, in some embodiments, a composition of the present invention comprises methacrylated gelatin (GelMa), heparin sulfate, chondroitin sulfate, alginate sodium salt, unmodified gelatin, elastin, non-thiolated hyaluronic acid, non-methacrylated collagen (e.g., Type I, II, III, and/or IV collagen), one or more components for modifying elastic modulus of the composition, one or more components for cell adhesion profile modification, one or more components for tissue-specific biochemical modification, and/or one or more small molecules (e.g., a small molecule that can has additional cross-linking capability and/or can provide hydrogen bonding and/or non-covalent complexing).

In some embodiments, a composition of the present invention comprises a protein (e.g., an adhesion protein) and/or proteoglycan, optionally a modified protein and/or modified proteoglycan. In some embodiments, the protein and/or proteoglycan may be modified with one or more functional group(s), such as, e.g., modified with a maleimide, that can bind and/or crosslink to thiolated hyaluronic acid, non-thiolated hyaluronic acid, methacrylated collagen, and/or non-methacrylated collagen. In some embodiments, a composition of the present invention comprises fibronectin, heparin, and/or laminin, optionally a modified fibronectin, heparin, and/or laminin (e.g., modified with a maleimide), or other cell adhesion protein(s) and/or or cell adhesion protein peptide derivative(s).

One or more growth factor(s) may be present in a composition of the present invention. In some embodiments, the composition comprises one or more growth factor(s) that are linked and/or bound by a heparin pendant chain. The one or more growth factor(s) may be appropriate for the particular cells that may be present in and/or added to the composition and/or for the particular tissue dimensional tissue construct being produced. In some embodiments, growth factors and/or other growth promoting proteins may be provided in a decellularized extracellular matrix composition (ECM) from a tissue corresponding to the tissue cells (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; etc.). Additional collagens, glycosaminoglycans, and/or elastin (e.g., which may be added to supplement the extracellular matrix composition), etc., may also be included.

In some embodiments, a composition of the present invention may be customized to match the biochemical profile of one or more (e.g., 1, 2, 3, 4, 5, or more) tissue(s) (e.g., a tissue found in a mammalian body). In some embodiments, an adhesion protein such as, e.g., one found in a particular tissue, may be synthetically modified to allow for direct coupling to a component in the composition (e.g., the thiolated hyaluronic acid and/or methacrylated collagen). Growth factors may be linked through heparin pendant chains Fibronectin, laminin, and/or other adhesion proteins may be synthetically modified to have one or more chemical group(s) that crosslink directly into a component in the composition (e.g., the thiolated hyaluronic acid and/or methacrylated collagen), which may allow for tissue-specific customization. In some embodiments, inclusion of covalently linked fibronectin in the composition may have a significant influence in maintaining function of a three-dimensional tissue construct formed and/or provided in the composition (e.g., a liver organoid).

A composition of the present invention may have a pH of about 6, 6.5, or 7 to about 7.5 or 8. In some embodiments, the composition has a pH of about 6, 6.5, 7, 7.5, or 8. In some embodiments, when the composition has a pH below 7, the composition is in liquid form. In some embodiments, when the composition has a pH at or above 7, the composition is in the form of a gel, optionally an extrudable gel.

A composition of the present invention may be self-supporting (i.e., the composition can support its own weight such as, e.g., after deposition onto a substrate) and may be devoid of a sacrificial support material. In some embodiments, the composition may support two or more (e.g., 3, 4, 5, 6, 7, 8, 9, 10 or more) layers of the composition that are deposited onto a prior layer, optionally wherein one or more (or all) of the layers has a height of about 1 mm or less such as, e.g., about 0.9, 0.8, 0.7, 0.6, 0.5, 0.4, 0.3, 0.2, or 0.1 mm. In some embodiments, a composition of the present invention can support one or more (e.g., 2, 3, 4, 5, 6, 7, 8, or more) channel structures formed therefrom. The channel structure may have a diameter in a range of about 0.1 mm to about 2 cm and/or a length of about 0.1 mm to about 5 cm. In some embodiments, a channel structure may have a diameter of about 0.1, 0.25, 0.5, 0.75, or 1 mm to about 1.5, 2, 2.5, 3, 3.5, 4, 4.5, or 5 mm and/or a length of about 0.1, 0.25, 0.5, 0.75, 1, or 5 mm to about 10, 15, 20, 25, 30, 35, 40, 45, or 50 mm. In some embodiments, a channel structure may have a diameter of about 1, 2, 3, 4, 5, 6, 7, 8, or 9 mm to about 10, 11, 12, 13, 14, 15, 16, 17, 18, 19, or 20 mm and/or a length of about 1, 2, 3, 4, 5, 6, 7, 8, 9, 10, 11, 12, 13, 14, 15, 16, 17, 18, 19, or 20 mm to about 25, 30, 35, 40, 45, or 50 mm.

In some embodiments, a composition of the present invention is deposited onto a surface and forms a construct. The construct may be dried. In some embodiments, the construct (that is optionally wet or dry) is contacted with and/or submerged in a liquid such as, but not limited to, an aqueous solution, a hydrogel, and/or cell culture media. In some embodiments, a composition of the present invention is deposited into a composition (e.g., a gelatin composition and/or cell culture media) and forms a construct. The construct (wet or dry) may have a height, width, and/or length of about 0.1, 0.5, 1, 5, or 10 mm to about 1.5, 2, 3, 4, 5, 6, 7, 8, 9, or 10 cm. In some embodiments, the construct (wet or dry) may have an aspect ratio (height/width) of about 1, 2, 3, or 4 to about 5, 6, 7, 8, 9, or 10. In some embodiments, the construct (wet or dry) may have an aspect ratio (height/width) of at least about 1, 2, 3, 4, 5, 6, 7, 8, 9, or 10.

A composition of the present invention may be biocompatible (optionally with two or more different cell types) and/or printable. In some embodiments, the composition is extrudable (e.g., from a syringe and/or bioprinter). In some embodiments, the composition is extrudable through a 19.5, 20, 22, 23.5, or 30.5 Gauge needle, optionally at room temperature and/or pressure. The composition may be liquid upon extrusion and after extrusion may be solid. A composition of the present invention (e.g., a bioink) may be stable and solid under normal conditions, but is printable and can transition between a solid-like behavior at rest, and a liquid-like behavior during printing. In some embodiments, a composition of the present invention is thixotropic. Thixotropism is a material characteristic that is a special case of shear thinning, and refers to the material's ability to behave like a solid under low shear conditions and behave like a liquid under high shear conditions. In some embodiments, a composition of the present invention remains a solid while in a syringe, behaves like a liquid when subjected to the high shear environment of extrusion through the nozzle and/or needle of the syringe, and then regains its solid like characteristics upon deposition (e.g., onto a surface of a substrate and/or into a composition). In some embodiments, a composition of the present invention is thixotropic, can retain its shape following deposition (e.g., extrusion from a syringe and/or printer), and can support two or more layers of the composition.

A composition of the present invention may have an elastic modulus (i.e., stiffness), at room temperature and atmospheric pressure, that is sufficiently low such that the composition can be manipulated and/or deposited onto a substrate and/or into a composition by whatever deposition method is employed (e.g., extrusion deposition, bioprinting, etc.). The elastic modulus, again at room temperature and atmospheric pressure, of the composition may be sufficiently high so that the composition will substantially retain the shape and/or configuration in which it is deposited, optionally until subsequent cross-linking (whether that cross-linking be spontaneous, thermal or photo-initiated, etc.).

In some embodiments, a composition of the present invention may have an elastic modulus (E'), prior to and/or after deposition and/or optional subsequent crosslinking, from about 0.05, 0.1, 0.5, 1, 1.5, or 2 kiloPascals (kPa) to about 2.5, 5, 10, 15, 20, 25, 50, or 100 kPa at room temperature and atmospheric pressure. In some embodiments, a composition of the present invention may have an elastic modulus (i.e., stiffness) from about 0.01, 0.025, 0.05, or 0.1 kiloPascals to about 0.5, 1, 5, 10, 15, 20, or 25 kiloPascals, or more, at room temperature and atmospheric pressure. In some embodiments, the composition, prior to deposition and/or optional subsequent crosslinking, has a stiffness of from about 10 or 25 Pascals (Pa) to about 500 Pa at room temperature and atmospheric pressure. In some embodiments, the composition, prior to deposition and/or prior to optional subsequent cross-linking, has a stiffness of about 10, 25, 50, 75, 100, 150, 200, 250, 300, 350, 400, 450, or 500 Pascals at room temperature and atmospheric pressure. In some embodiments, the composition, after deposition and/or after optional subsequent cross-linking, has a stiffness from about 0.1 kPa to about 25 kPa at room temperature and atmospheric pressure. In some embodiments, the composition, after deposition and/or after subsequent cross-linking, has a stiffness of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25 kPa at room temperature and atmospheric pressure. A composition of the present invention may mimic the elastic modulus of a tissue in vivo. In some embodiments, a composition of the present invention has an elastic modulus value that is substantially the same as (i.e., within ±20% of) the elastic modulus value of a tissue in vivo.

A composition of the present invention may have an elastic modulus after extrusion and/or bioprinting that varies by less than about ±20% compared to an elastic modulus of the composition prior to extrusion and/or bioprinting. In some embodiments, the composition may have an elastic modulus (G') and a loss modulus (G") that are within about ±20%, 15%, 10%, or 5% of each other or less. In some embodiments, a composition of the present invention is thixotropic.

A composition of the present invention may be extrudable. For example, in some embodiments, the composition may be extrudable from a syringe and/or bioprinter. In some embodiments, the composition may be extruded with an applied mechanical stress in a range from about 5 kPa to about 80 kPa. In some embodiments, the composition may be extruded with an applied mechanical stress of about 5, 10, 15, 20, 25, 30, 35, 40, 45, 50, 55, 60, 65, 70, 75, or 80 kPa.

Some embodiments of the present invention are directed to a method of making a three-dimensional construct (e.g., a scaffold, a three-dimensional tissue construct, and/or an organoid). The method may comprise depositing a composition of the present invention onto a surface of a substrate and/or into a composition, thereby forming the three-dimensional construct. A composition of the present invention may be deposited onto a surface and/or into a composition using methods known to those of skill in the art such as, but are not limited to, inserting, injecting, adding, pouring, printing, extruding, and/or the like such a composition of the present invention onto a surface and/or into a composition. In some embodiments, a composition of the present invention is deposited using a syringe, pipette, needle, and/or printer (e.g., via a printhead). In some embodiments, a composition of the present invention is deposited using a syringe and/or printer. Exemplary printers include, but are not limited to, bioprinters commercially available from Allevi and/or bioprinters commercially available from Cellink such as, e.g., the INKREDIBLE+ 3D bioprinter, e.g., by extrusion through a syringe). In some embodiments, a composition of the present invention is deposited via extrusion based bioprinting. In some embodiments, a composition of the present invention is deposited into a composition such as, e.g., a gelatin composition such as, e.g., described in U.S. Provisional Application Ser. No. 62/715,548 filed Aug. 7, 2018, the contents of which are incorporated herein by reference in their entirety. A gelatin composition (e.g., a gelatin solution) may have a gelatin concentration of about 1 mg/mL to about 20 mg/mL.

A method of the present invention may comprise crosslinking a composition of the present invention during and/or after the depositing step. In some embodiments, the crosslinking is performed to increase the stiffness of the composition, optionally after deposition.

In some embodiments, a composition of the present invention is deposited (e.g., printed) without the use of a support material (e.g., a scaffold) and/or a three-dimensional tissue construct is formed without the use of a support material. In some embodiments, the deposited three-dimensional construct serves as a scaffold for one or more cells that are subsequently contacted to the three-dimensional construct and/or cultured in the presence of the three-dimensional construct.

In some embodiments, a composition of the present invention is deposited in the form of a shape such as, e.g., a spheroid and/or a shape resembling a natural tissue or portion thereof. In some embodiments, the deposited composition is in the form of a shape or structure that includes one or more (e.g., 2, 3, 4, 5, 6, 7, 8, 9, 10, or more) channel(s). In some embodiments, the deposited shape, optionally including one or more channel(s) is retained after deposition. In some embodiments, the deposited three-dimensional construct is a three-dimensional tissue construct. In some embodiments, the deposited three-dimensional construct is an organoid. In some embodiments, the deposited three-dimensional construct is in the form of a tissue comprising one or more blood vessels, optionally wherein the construct comprises two or more different cell types. In some embodiments, the deposited three-dimensional construct is implantable.

In some embodiments, the deposited three-dimensional construct is cultured for one or more day(s) (e.g., 2, 3, 4, 5, 6, 7, 10, 14, 21, 32, or more days) in the presence of cell culture media, optionally wherein the cell culture media comprises cells.

In some embodiments, a composition and/or method of the present invention comprises increasing the viability and/or functional activity of a three-dimensional tissue construct (e.g., an organoid), optionally compared to the viability and/or functional activity of a three-dimensional tissue construct not in accordance with a composition and/or method of the present invention. The method may comprise providing a composition of the present invention comprising live cells and/or preparing a three-dimensional tissue construct according to a method of the present invention, and optionally culturing the three-dimensional tissue construct in the composition.

A composition and/or method of the present invention may comprise and/or provide one or more (e.g., 1, 2, 3, 4, 5, 6, 7, 8, or more) different three-dimensional tissue construct(s) (e.g., organoid(s)) that each are viable for at least 1, 2, 3, 4, or more weeks. In some embodiments, a composition and/or method of the present invention may comprise and/or provide one or more three-dimensional tissue construct(s) that are viable and may comprise at least about 75% or more (e.g., about 80%, 85%, 90%, 95% or more) living cells based on the average number of cells present in the three-dimensional tissue construct(s) at 1, 2, 3, 4, or more weeks (e.g., in culture in the composition). The three-dimensional tissue construct may be generated by differentiation from a common cell sample (e.g., a sample such as a skin or tumor biopsy sample collected from a subject). The three-dimensional tissue construct may comprise cells in proportions similar to the proportions of cells present in the corresponding native (e.g., human) tissue. In some embodiments, the three-dimensional tissue construct comprises diseased cells. In some embodiments, the three-dimensional tissue construct comprises metastatic and/or malignant cells. In some embodiments, a function and/or property of the three-dimensional tissue construct may be determined and/or measured and compared to the function and/or property of a corresponding native tissue (e.g., a property of a liver three-dimensional tissue construct may be measured and compared to the same property of a liver tissue in a subject). In some embodiments, a function and/or property of the three-dimensional tissue construct may be similar to the function and/or property of a corresponding native tissue.

In some embodiments, a composition and/or method of the present invention can achieve a take rate of at least 50% or more such as, e.g., about 50%, 55%, 60%, 65%, 70%, 75%, 80%, 85%, 90%, 95%, 98%, or more. For example, a 90% take rate means that 90% of the time a viable three-dimensional tissue construct or plurality of three-dimensional tissue constructs (e.g., an organoid set) is achieved and/or provided by a method of the present invention. That is, for a 90% take rate, 9 out of 10 cell samples (e.g., tumor cell samples) yield a viable three-dimensional tissue construct or plurality of three-dimensional tissue constructs when prepared according to a method of the present invention.

The foregoing and other aspects of the invention are explained further in the following examples.

EXAMPLES

Example 1

Gelatin nanoparticles were added to a bioink based on a UV crosslinkable methacrylated collagen and hyaluronic acid hydrogel. With the gelatin nanoparticle addition, the hydrogel bioink became a thixotropic bioink capable of retaining its shape once extruded and supporting multiple layers, allowing for constructs to have substantial height.

Materials

Methacrylated collagen was purchased from Advanced Biomatrix. Heprasil was purchased from ESI BIO. Hyaluronic acid (HA), gelatin type B 225 bloom, 25% glutaraldehyde, Irgacure 2959, and acetone were all purchased from Sigma Aldrich. 12M hydrochloric acid was purchased from Fisher Scientific. Dulbeccos phosphate buffered saline (DPBS) was purchased from Hyclone. Deionized (DI) water was obtained from an in house source. All materials were used without further purification.

Methods

GNP Synthesis

Gelatin nanoparticles (GNPs) were synthesized using a two step desolvation method developed by Coester et al, with some modifications. Briefly, 2.5 g gelatin was dissolved in 50 mL DI water at 40° C. under stirring. Once dissolved, 50 mL of acetone was added in one dose to precipitate the gelatin. The solution was taken off heating and stirring, and left to cool for 1 hr. to drop the high molecular weight gelatin out of solution. The supernatant was then decanted. The remaining solid gelatin was redissolved in 50 mL DI water at 40° C. under stirring. The pH was changed to 2.5 with 12M HCl. 150 mL of acetone was then dripped in at 5 mL/min while the solution was heated at 40° C. and under vigorous stirring. Once the all of the acetone was added, 200 µL of glutaraldehyde was added to crosslink the nanoparticles. The solution was left to stir under heating for 2 hrs. Then, the solution was moved to four 50 mL centrifuged tubes. The pH of each of the solutions was changed to 3.5 to precipitate the GNPs. The tubes were first centrifuge for 2 minutes at 1000 RPM to pelletize the GNPs. The GNPs were washed by decanting the supernatant, redispersing with 15 mL DPBS, and centrifuging at 3500 RPM for 15 minutes. This washing procedure was done a total of three times to each sample. After the final centrifugation step, the conicals were placed in a −20 C freezer over night, and then lyophilized for 3 days. The dried GNPs were then finely powderized with mortar and pestle. The resulting powder was stored at room temperature until further use. Any GNPs that needed to be sterile were done so using 10 Mrad of gamma irradiation per gram of GNPs.

SEM Analysis

Once the GNPs were lyophilized, sections of the solid pellet were broken off and placed on an aluminum stand covered in carbon tape for SEM analysis. The GNP samples were gold sputtered coated before being imaged. Micrographs were taken on a Hitachi FlexSEM 1000, and the sputter coating was done on a Leica EM600.

Bioink Production

Previous data gathered by our group has shown that a UV-crosslinkable hydrogel made of 3 parts 6 mg/mL methacrylated collagen with 1 part 10 mg/mL Heprasil and 250 µg/mL Irgacure is capable of supporting a variety of cell types, without any issues from the UV crosslinking event. This will be the basis for the model material. Gelatin and hyaluronic acid were tested for the support material. The model material had various concentrations of GNPs added, and each sample was mechanically analyzed via a strain sweep on a TA DHR rheometer with roughened 25 mm 2° cone and plate geometry. The samples were analyzed both before and after crosslinking. The support materials were analyzed in the same way, but both the hydrogel concentration and GNP concentration were varied and analyzed to find the formulation that was best for printing.

Printability

Qualitative printing studies were done to determine the best parameters for printing large hollow structures. The main parameters investigated were nozzle diameter, printing pressure, printing speed, and layer height. The printed structures were qualitatively analyzed base on their ability to flow continuously from the nozzle and retain structure once printed. The structure to be printed, CAD model shown on the right in FIG. 1, determines how well the gel supports itself, and what size features can be made in the X, Y, and Z direction.

Disk Production

Disks made of the collagen, Heprasil, and GNP bioink (CHG bioink) were made by combining the previously described UV-crosslinkable methacrylated collagen and Heprasil hydrogel with GNPs. This CHG bioink was then formed into disks 8 mm in diameter and 0.5 mm in height using glass slides and a silicone mold. Each disk was then crosslinked with 356 nm UV light for 20 s. These disks were used for biocompatibility and mechanical studies.

Biocompatibility

Disk constructs 8 mm in diameter and 0.5 mm thick were made with 10 M/mL cells, and crosslinked with UV light for 20 sec. These disks were then used for live/dead and DAPI staining as well as MTS assays to determine biocompatibility. The staining and assays were done on day 0, 1, 5, and 14.

Results and Discussion

GNP Synthesis

Figure 2:
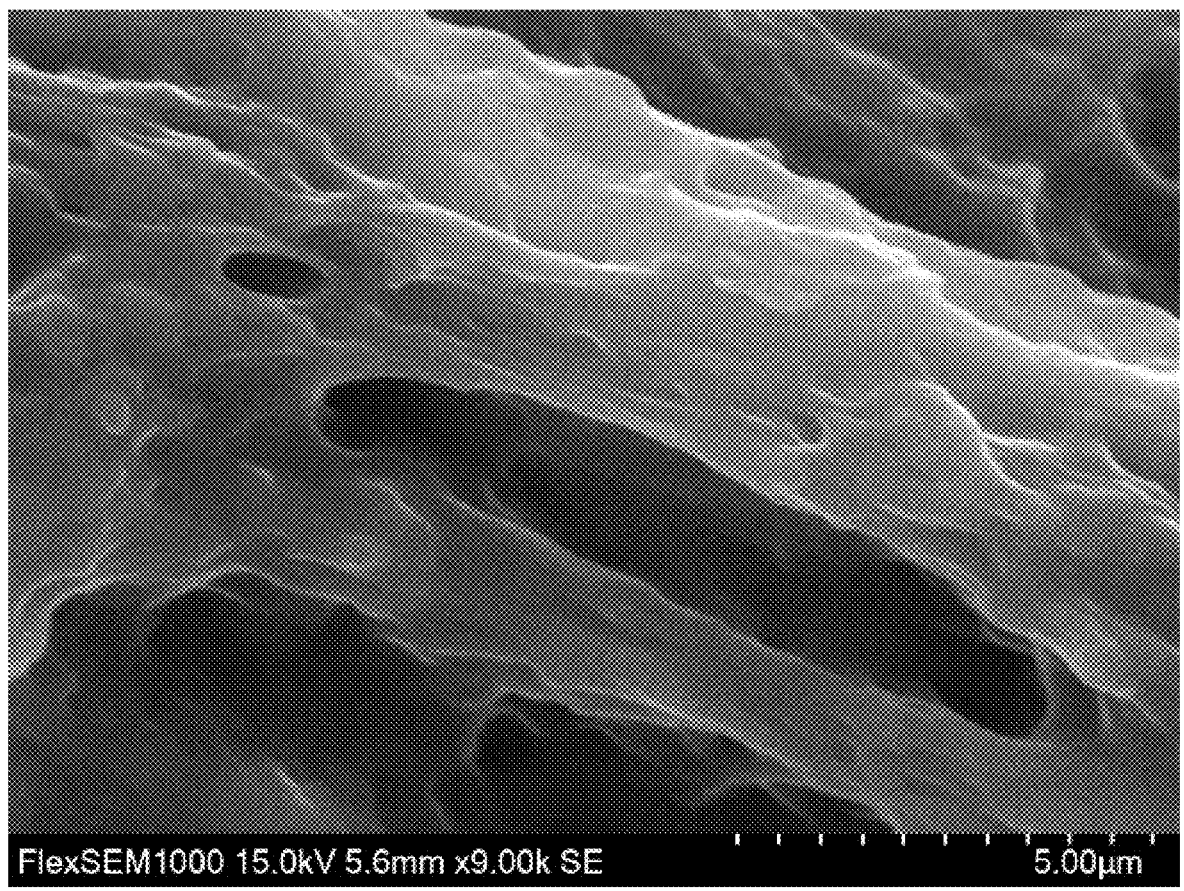
FIG. 2 is a SEM micrograph image showing GNP aggregates within a free gelatin matrix.

The nanoparticles were confirmed to be made SEM analysis, shown in FIG. 2. The SEM micrograph shows GNPs of 300 nm average diameter aggregated together and embedded in free gelatin left over form processing.

Bioink Mechanics

Figure 3:
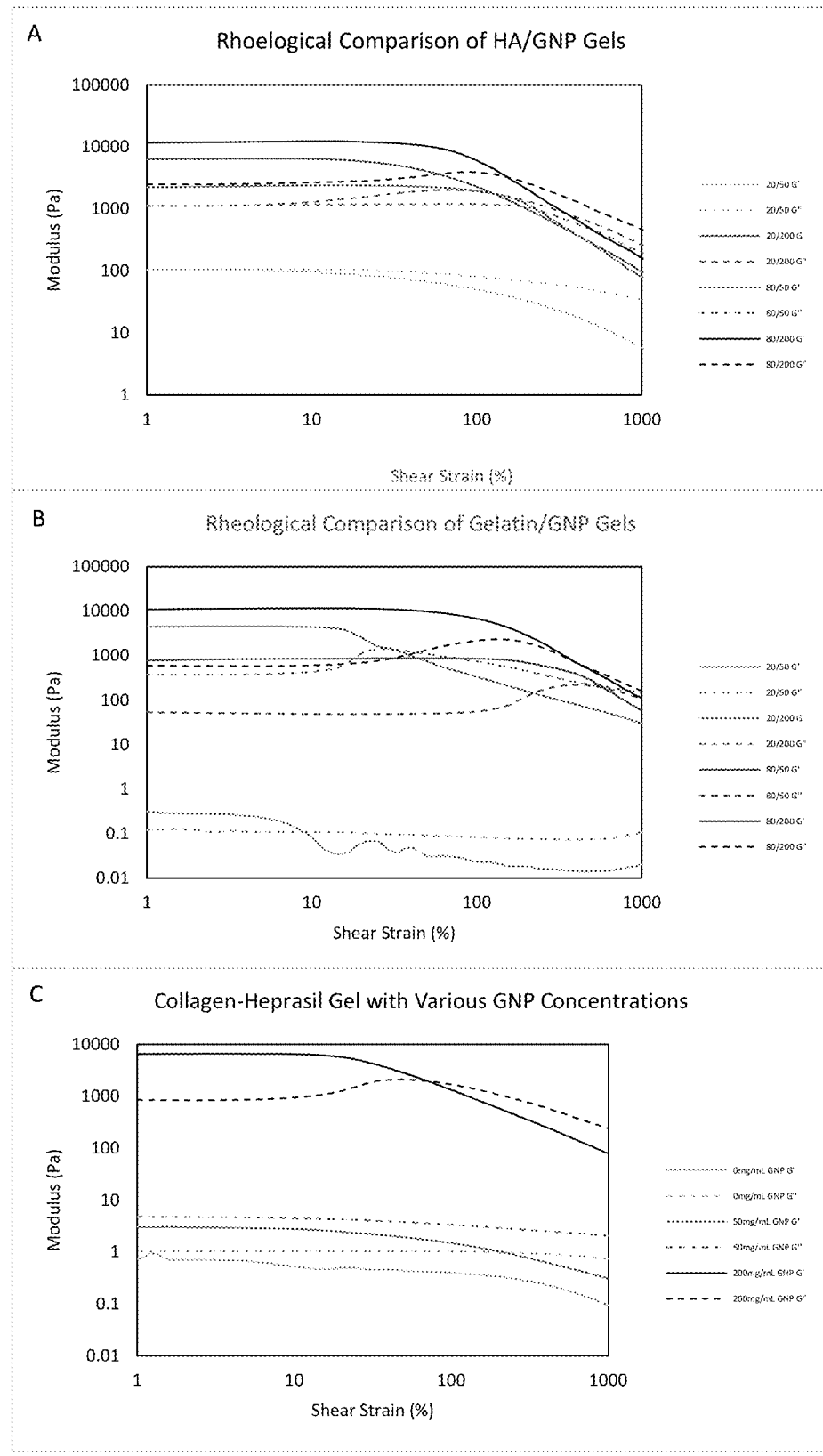
FIG. 3 shows graphs of rheology data for different bioinks made with GNPs and A) HA, B) gelatin, and C) collagen and Heprasil.

GNP addition to gelatin, HA, and Col/Hep gels were able to induce a strong thixotropic behavior, at high concentrations, in all of the tested materials. FIG. 3 shows the rheological responses to changes in hydrogel and GNP concentrations. The thixotropic nature is represented by G' and G" crossing with increasing shear strain. Before this point, the solid like characteristics of the bioink dominated, and the material behaves as a solid. Beyond this point, which is a high shear environment, the material deforms readily and behaves as a liquid. When the shear is removed, the solid like behavior is quickly restored. The liquid like behavior at high shear will be the behavior seen when the material is pushed through a printing nozzle.

While all of the tested hydrogel/GNP inks tested were confirmed to be thixotropic, not all of them were self supporting. At low concentrations of both matrix material and GNPs, the material response appears solid like, as determined by rheology. However, qualitative analysis using simple hand extrusion through a syringe shows that the material still oozes once extruded. There is some threshold value of G' where anything below it is going to ooze, even if the rheology shows that G' is higher than G".

Biocompatibility

Figure 4:
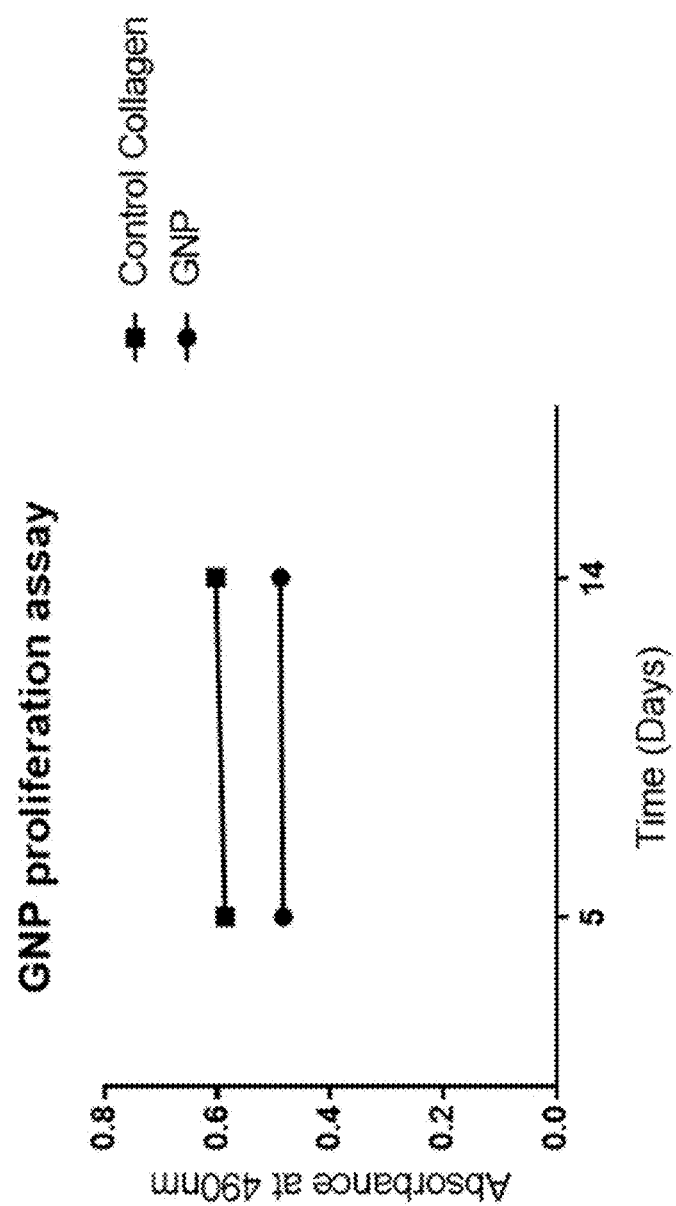
FIG. 4 is a graph providing MTS results between the standard collagen/Heprasil gel and the GNP bioink at day 5 and 14.

Staining and imaging the disk samples was difficult due to the opacity of the disks. The disks could only be visualized about 100 µm deep. Live/dead assays show significant cell death at day 0, right after mixing the cells with the gel and forming the disks. This is most likely due to cells acclimating to their environment, but the high shear environment of mixing the cells into this paste and the constructs drying while being formed may have also contributed. As the constructs were cultured, they were shown to sustain cell numbers, confirmed again by live/dead assays at day 1, 5, and 14. Biocompatibility was also confirmed with MTS assays at days 1, 5, and 14. These results can be seen in FIG. 4. These results show that the constructs sustained cell viability, but little proliferation seen.

Printability

Figure 5:
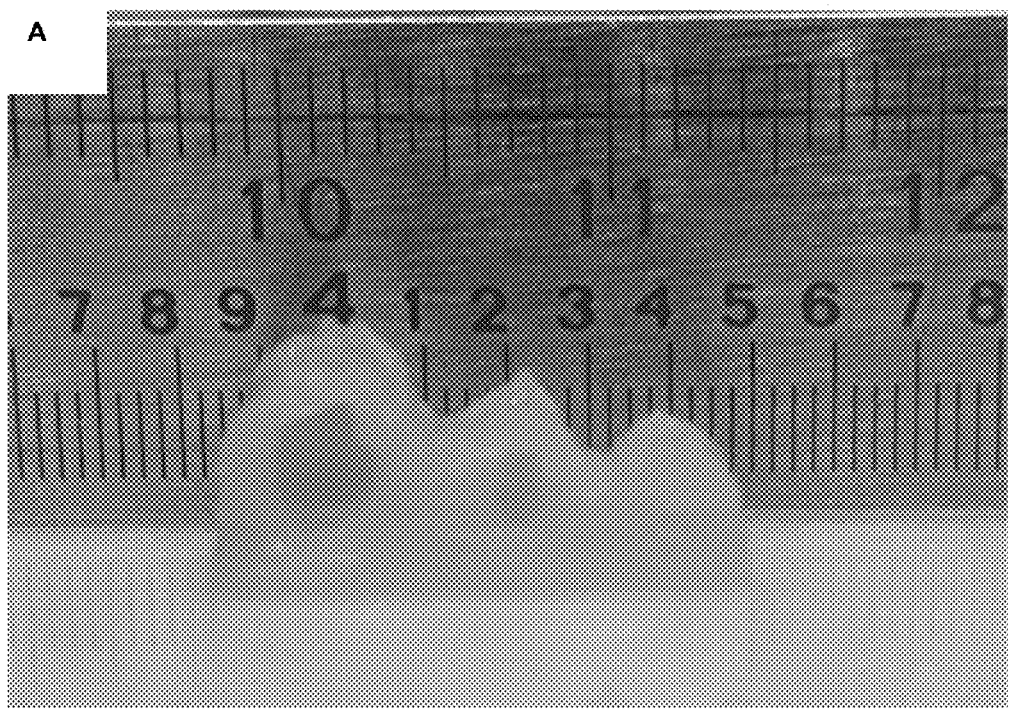
FIG. 5 shows images of A) a front and B) top view of a construct prepared with a gelatin/GNP bioink including 40 mg/mL gelatin and 150 mg/mL GNP, according to some embodiments of the present invention, that exhibits greatly improved printability. This bioink was able to produce large hollow structures (e.g., channels) of 1/8", 1/16", and 1/32" at a precision of 0.05" on a commercially available bioprinter, the Cellink Inkredible printer.
Figure 5:
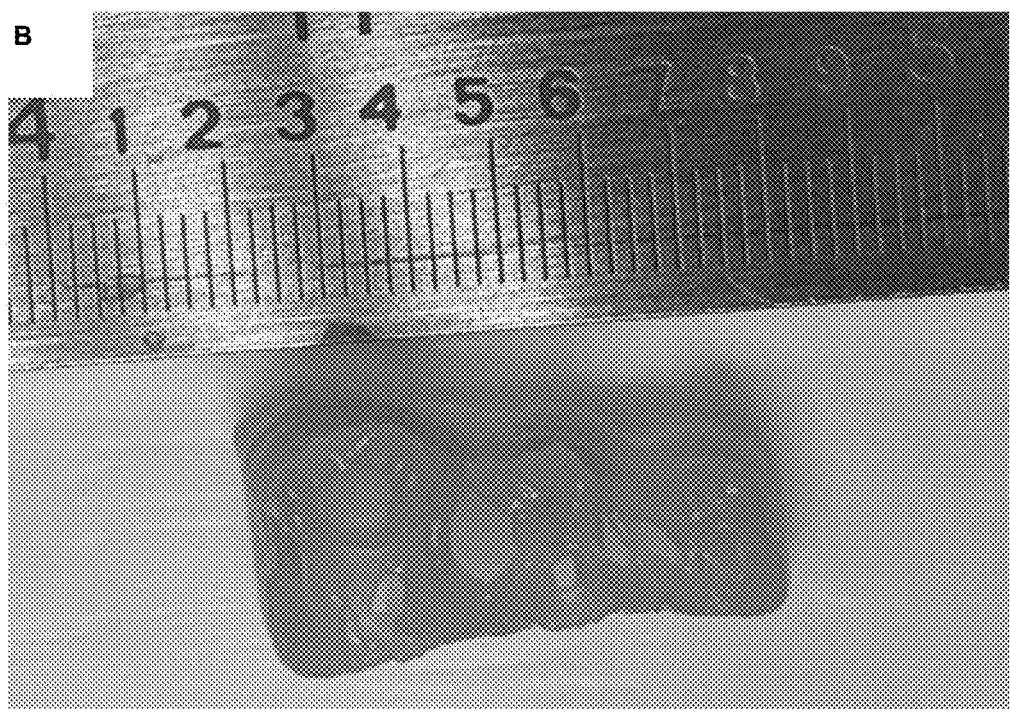

The GNPs added to hyaluronic acid, gelatin, or the collagen/Heprasil base hydrogel creates printable inks that are capable of supporting their own weight. Shown in FIG. 5 is a construct made with 40 mg/mL gelatin and 150 mg/mL GNPs, which was the best support material formulation. At these concentrations, with a 20 Ga nozzle, 150 kPa print pressure, 0.2 mm layer heights, and 10 mm/s print speed, large hollow structures can be achieved with minimal clogging. Decreasing the concentration causes the material to not be strong enough to support itself. Increasing the concentration causes the printing pressure to be too great and increases clogging. There is some flexibility with print speed and layer height where these values can be changed slightly with little to no change in resolution. Decreasing the nozzle diameter would increase resolution, but clogging occurred too frequently to reproducibly create large hollow constructs. The CHG bioink with 200 mg/mL GNPs had similar printability, data not shown.

These two materials, when used in tandem, can be used to create even larger constructs with thin walls. The CHG bioink would act as a model material, and the gelatin/GNP bioink would act as a support material to hold the CHG bioink in place. Once printed, the whole piece would be cured under UV light, and only the CHG bioink would solidify. This allows for the gelatin/GNP bioink to be washed away using warm water to reveal a solid model made of the CHG bioink.

We have shown the creation of thixotropic hydrogels for bioprinting, called bioinks, by using GNPs as a thixotropic inducing material. This suggests that any hydrogel material can be turned into a thixotropic hydrogel with the addition of sufficient GNPs. Any biocompatible hydrogel system will not be affected by the addition of GNPs, though care should be taken to not add too many as an overabundance of GNPs in a hydrogel may remove too much water from the system, causing cell death. Also, if the GNP content is too high, it may create a very stiff gel. Cells can rupture when being incorporated into stiff gels due to the high shear environment caused by mixing. We found that a GNP concentration of around 150 mg/mL was ideal for bioink function. This concentration created separate printable gels made from gelatin, HA, and a Col/Hep mixture. Chemical modifications to GNPs, including various functionalizations as well as drug loading, will have little effect on the overall size of the GNPs, and thus should be able to be added to hydrogels in a similar fashion to produce chemically active bioinks. Based on our findings, we believe that GNPs can be used as an additive to any biomaterial hydrogel to create an effective bioink.

Example 2

Bioinks including GNPs have demonstrated the ability to support channel structures within the printed constructs from the bioinks. This is a very important feature in tissue engineering as a whole. Briefly, if a tissue engineered construct is to be of any significant size, channels (or vasculature) will be needed as the diffusion limit in such constructs is generally less than 500 microns. Studies were performed to verify that bioinks including GNPs have the mechanical properties required to support channel structures without collapsing in on themselves. Towards this effort, several 3D constructs with channels were created as shown in FIG. 6, which demonstrate that such bioinks have the requisite mechanical properties to support channel structures without collapsing in on themselves.

Figure 6:
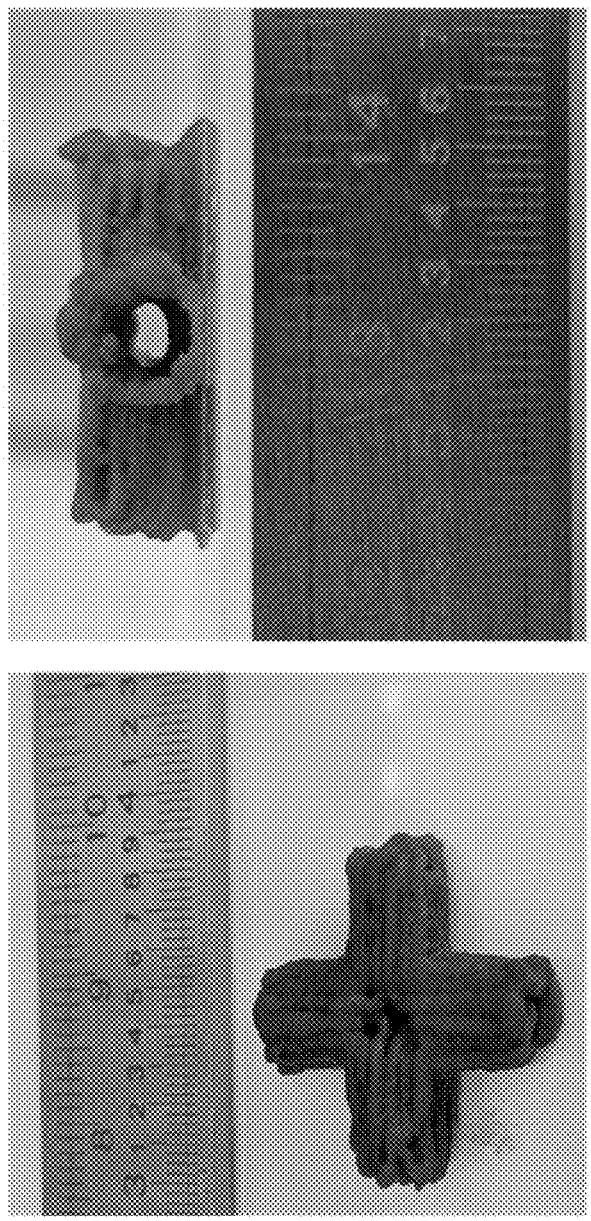
FIG. 6 shows images of a A) top and B) side view of a construct prepared with a bioink including hyaluronic acid, collagen, and gelatin nanoparticles. The construct was able to be precisely printed and had sufficient strength in that the structure did not collapse or sag, even when tilted sideways.

As shown in FIG. 6, constructs with intricate features were printed to showcase the ability of the bioink to be self-supportive. Conditions were: 20 Ga needle, tip diameter of 1.2 mm, ~130 kPa pressure, 12 mm/s print speed, and 0.5 mm layer height. The prints are repeatable.

Example 3

GNPs were made by a processing method that included a rotor evaporation step. This method created a smoother, yet still thixotropic, bioink that was able to be extruded through very fine nozzles with little to no clogging. A 30½ Ga needle was used to extrude GNP bioink onto the surface of a glass slide and create a hollow column structure from the bioink. The bioink was 40 mg/mL gelatin and 150 mg/mL GNPs in DI water. This bioink can be extruded by hand only with this fine of a tip. The Inkredible printer does not produce enough pressure to extrude this bioink with this fine of a nozzle. Pressures >350 kPa are needed.

The process for preparing the GNPs was as follows: 2.5 g gelatin is dissolved in 50 mL DI water at 40 C and vigorous stirring, 50 mL acetone is dumped in and the solution is taken off heating and stirring to allow the high molecular weight gelatin to precipitate, the supernatant is then decanted, the precipitate is dissolved in 50 mL DI water at 40 C and vigorous stirring, the pH is changed to 2.5 with 12M HCl, 150 mL acetone is dripped in at 10 mL/min while being stirred and heated, 200 µL glutaraldehyde is added to crosslink the nanoparticle, the solution is left under heating and stirring overnight to react, the solution is then rotor evaporated until all acetone is removed, the pH is then shifted to 7 with 1M NaOH, the solution is then centrifuged at 35,000 RPM in a Sorvall T890 rotor for 15 minutes to collect the GNPs, the pellet is then redispersed in PBS, this centrifugation and redispersion process is done two more times to wash the GNPs, the GNPs are centrifuged one last time, the pellets are collected and frozen at −80 C, the frozen pellets are then lyophilized for at least 3 days, the resulting material is then powderized with mortar and pestle and ready for use in bioinks. A future step of cryomilling to powderize the GNPs is being explored.

Example 4

A GNP bioink made with 40 mg/mL gelatin, 150 mg/mL GNP, and 1 mg/mL Irgacure 2959 was formed into a disk shape using a silicone mold. A cross shaped extrusion made of UV curable collagen/Heprasil bioink was placed, by hand, into the GNP bioink and allowed to soak in briefly. The excess bioink was then blotted away with a paper towel. The structure was then exposed to 10 seconds of intense UV light to crosslink the collagen bioink. The structure was then placed in warm water to dissolve away the GNP bioink, leaving the cured collagen bioink structure. After crosslinking, but before dissolution, the cross structure was not visible. In contrast, after dissolution, the cross structure was visible and detached from the dissolved GNP bioink support. This confirms that bioinks including GNPs can be used as model and/or support materials, and it confirms the idea of inkjetting into a GNP bioink to create ultrafine structures. While not wishing to be bound to any particular theory, if inkjetting was coupled with extrusion printing, the extrusion printing could lay down the majority of the volume and support, and the inkjetting would lay down the highly detailed structures. The support material could then be removed with warm water allowing the extra fine model to be safely collected.

Example 5

To examine relationships between nozzle size, print pressure, and speed, three different nozzle sizes were chosen, 19½ Ga, 22 Ga, and 23½ Ga. These roughly decrease in cross sectional area by 2. Speed was changed between 10 mm/s and 20 mm/s. The printer cannot move much faster than 20 mm/s, and 10 mm/s is a typical speed. Pressure was then adjusted on the fly until smooth high definition prints were obtained. The GNP bioink was unable to extrude from the 23½ Ga needle because the printer could not handle that high of a pressure. Every test print was a multilayered square shape. The GNP bioink performed better than a bioink including thiolated HA and thiolated gelatin that was crosslinked with PEGDA and PEG-alkyne. Table 1 shows the nozzles and speeds with the required pressure for a bioink include 40 mg/mL GNPs, 150 mg/mL gelatin, and water.

TABLE 1

Print properties for a GNP bioink.

| Nozzle (Ga) | Speed (mm/s) | Pressure (kPa) | Notes |
| --- | --- | --- | --- |
| 19.5 | 10 | 55 | High definition |
| 19.5 | 20 | 75 | smooth printing |
| 22 | 10 | 180 | |
| 22 | 20 | 190 | |
| 23.5 | 10 | >300 | Not possible, too high of pressure needed |

Example 6

Base Bioink Formulation

The base bioink composition is made from methacrylated collagen (Advanced BioMatrix, Carlsbad, Calif.), initially dissolved in sterile filtered 20 mM acetic acid solution (Advanced BioMatrix) at 6 mg/mL. This solution was kept refrigerated at 4° C. until needed. When ready for use, aliquots were removed and neutralized with a neutralization solution (Advanced BioMatrix), which was sterile filtered before use, according to the manufacturer's protocol: 85 µL per mL of 6 mg/mL methacrylated collagen dissolved in the 20 mM acetic acid solution. Thiolated HA (Heprasil, ESI BIO, Alameda, Calif.) was dissolved at 10 mg/mL with deionized (DI) water provided from an in-house supply with 1 mg/mL of Irgacure 2959 (Sigma-Aldrich, St. Louis, Mo.), added as the photoinitiator for UV crosslinking. The ColMa and HA solutions were then mixed in a 3:1 ratio by volume prior to use.

Gelatin Nanoparticle Preparation

Gelatin nanoparticles (GNPs) were made using a process based on the two-step desolvation method originally developed by Coester et al. Briefly, 2.5 g gelatin type B, 255 bloom (Sigma-Aldrich, St. Louis, Mo.) was dissolved in 50 mL DI water at 40° C. with vigorous stirring. Then, 50 mL acetone (Sigma-Aldrich) was added. The solution was removed from the stir plate and left to sit at room temperature for one hour to allow high molecular weight gelatin to precipitate. After the hour, the supernatant was decanted, and the remaining precipitated gelatin was redissolved in 50 mL DI water at 40° C. with vigorous stirring. The pH was adjusted to 2.5 using 12 M HCl and 10 M NaOH (Fischer Scientific, Hampton, N.H.). 150 mL of acetone was then added at a rate of approximately 5 mL/min. Once added, 800 µL of 25% glutaraldehyde in water (Sigma-Aldrich) was then added to the solution. The solution was gently stirred overnight at 40° C. to complete the reaction. The pH of the solution was then neutralized with 10 M NaOH which aggregated and precipitated the GNPs. These were then collected, redispersed in 200 mL Dulbecco's phosphate buffered saline (DPBS) (Thermo Fisher Scientific, Waltham, Mass.) to wash them of impurities. The solution was then centrifuged at 4600 RCF to collected the GNPs in a pellet. The redispersion in PBS and centrifugation process was performed two more times to wash the GNPs of any impurities. The final pellet was collected by redispersing it in a small amount of DI water. This pellet was then frozen overnight at −20° C., and then lyophilized for 3-5 days until completely dry. The resulting solid was then pulverized by hand with mortar and pestle and then cryomilled to powder the solid. The resulting powder was stored at room temperature in a water tight glass scintillation vial until further use.

GNP Analysis

Scanning electron microscopy (SEM) analysis was performed on a FlexSEM1000 (Hitachi, Schaumburg, Ill.) at 15 kV. The samples were prepared by placing some of the lyophilized GNPs on carbon tape, and then sputter coating the material with gold and palladium. The GNPs were also analyzed using dynamic light scattering (DLS) for size distribution and zeta potential ($\zeta°$) for aqueous stability using a Malvern Panalytical Zetasizer Nano Range (Malvern Panalytical, Malvern, United Kingdom). For each, the GNPs were added to the appropriate polystyrene cuvette immediately after synthesis, or after being dispersed in DI water after the cryomilling procedure, and then the analysis was performed. The GNP powder before and after cryomilling was observed under a Leica DMi1 (Leica Microsystems, Buffalo Grove, Ill.) microscope to compare their morphologies.

GNP Bioink Preparation

The GNP powder was sterilized by dry heating the powder at 100° C. for 30 minutes. They were then added, at various quantities, to the ColMA while it was still in acetic acid solution. This was mechanically stirred in to create a thick paste. This addition was performed at least two days prior to use, stirring frequently to completely hydrate and disperse the GNPs in the hydrogel. When ready to use, the ColMa and GNP material was neutralized as described above, and then the thiolated HA solution, prepared as described above, was added at the proper ratio. All concentrations of GNPs in the hydrogel bioink are reported as their final concentration in the complete hydrogel volume. The material was kept refrigerated at all times to prevent the collagen from forming fibers and to slow the spontaneous bonding of methacrylate groups with thiol groups.

GNP Bioink Mechanical Analysis

Once all components of the bioink were mixed, the bioink was analyzed using a TA instruments DHR-2 rheometer (TA Instruments, New Castle, Del.) with a 25 mm plate and 25 mm 2° cone system with 120 grit sandpaper intimately bonded to the surfaces. This addition mimics a roughened geometry for better adhesion to the bioink, preventing slippage during testing. Three analyses were performed: a strain sweep from 1% to 1000% shear strain ($\gamma$), a thixotropic analysis where alternating low strain (10% $\gamma$) and high strain (500% $\gamma$) was applied, and then a thixotropic recovery analysis where a strain pattern of low-high-low was performed. The strain sweep was performed to determine overall stiffness and elasticity of the bioinks along with the critical shear strain to induce a liquid transformation. The thixotropic analysis was performed to understand the reversible and repeatable behavior of the thixotropic mechanism. The thixotropic recovery analysis was performed to determine how much time was required for the bioink to regain all of its initial mechanics.

GNP Bioink Printing

The non-cellularized bioink underwent print testing using a CellInk Inkredible pneumatic bioprinter and a CellInk Bio X bioprinter with a syringe pump printhead (CellInk, Gothenburg, Sweden). All model prints were performed with a 3 mL BD Falcon syringe (Fischer Scientific) with a ½" 22 Ga blunt needle (CellInk, Gothenburg, Sweden) as the print nozzle, a print speed of 10 mm/s, a layer height of 0.2 mm, with single perimeter printing, no infill, and no supporting material. The pneumatic print head had pressure set around 250 kPa, adjusting for the heterogeneities in the bioink as they appeared during the print, while the syringe pump head was set to extrude at 0.75 µL/mm of printing. All 3D model architectures were developed in AutoDesk Inventor and sliced with Slic3r, or CellInk's onboard slicing software depending on the printer used.

GNP Bioink Swelling

Non-cellularized bioink was placed into a 8 mm×0.5 mm silicone mold and cured with UV light for 10 seconds. The disks were then removed, weighed, placed into 150 mm culture dish with 20 mm grid (Corning, Corning, N.Y.), and submerged in PBS. Top-down pictures were taken of the disks and the grid was used as a scale for image analysis using GIMP to determine diameter. The next day, the disks were again measured and weighed for comparison to their starting values.

Organoid Immersion Printing

Gelatin was sterilized by dry heating the material to 100° C. for 30 minutes, after which it was then dissolved at 40° C. in a sterile filtered solution of 1 mg/mL Irgacure 2959 dissolved in DI water, to reach a gelatin concentration of at 10 mg/mL. One mL of gelatin solution was then deposited into each well of a non-tissue culture treated Corning Falcon 48-well plate (Fischer Scientific). The plate was then placed in the refrigerator to cool overnight before bioprinting. When ready to print, the plate was placed in the Inkredible printer's print stage, which was then homed and calibrated, and then a specifically designed and sliced CAD file was created that instructed the printer to place one organoid per well. Each organoid was approximately 20 □L in volume. The print head nozzle was calibrated to a depth such that all extrusion would take place within the gelatin bath. All organoid printing was performed with the Inkredible in a 4° C. cold room to prevent the collagen component of the bioink from setting up as previously described. Once printed, the plate was exposed to a high intensity UV light for 10 seconds to permanently crosslink the organoids. Several plates of organoids were produced this way so that malformed organoids could be discarded, while still maintaining enough organoids for all subsequent studies.

Cell Culture

HepG2 cells (American Type Culture Collection, Manassas, Va.) were cultured using a media made of high glucose Dulbecco's modified eagle medium (DMEM, Fischer Scientific) supplemented with 10% fetal bovine serum (Sigma-Aldrich), 1% penicillin and streptomycin solution (Fischer Scientific), and 1% L-glutamine solution (Fischer Scientific) . Cells were incubated at 37° C. at 5% CO2 in Panasonic incubators (PHC Corporation of America, Wood Dale, Ill.). Cells were seeded into 150 mm Corning Falcon tissue culture plates (Fischer Scientific, Hampton, N.H.) at 2 million cells per plates, with 15 mL of media, and allowed to grow until confluent, swapping media every 2 days. Cell cultures were split by removing the media, washing twice with 2 mL DPBS, adding 7 mL of TrypLE solution (Thermo Fisher Scientific), and incubating for 5 minutes or until the cells were completely detached with gentle agitation. The TrypLE solution was then neutralized with 7 mL of culture media. The cell suspension was then collected and spun down in the previously mentioned centrifuge at 1100 RCF for 5 minutes. The supernatant was then discarded, and the cells were redispersed in 5 mL of media for counting. Cells were counted using a Nucleo View 200 automated cell counter (Cemometec, Allerod, Denmark). Cells were then reseeded at the previously described conditions for further culture.

Proliferation Study

Organoids were prepared as described previously with HepG2 cells at a cell density of 5 million per mL of bioink. The cells were first added to the thiolated HA, which was then mixed into the other bioink components as previously described. This cellular bioink was then loaded into pneumatically driven syringes (CellInk) as previously described for the organoid immersion printing method. Once printed and crosslinked, the plates were placed in the incubator until the gelatin immersion material was melted, about 15 minutes. The gelatin was then removed, and the each well was filled with 500 µL of media. The media was swapped every other day for the duration of the study. Before the media is added, the organoids undergo visual inspection to make sure none are too large (specifically, greater than 40 µL volume), organoids were fully crosslinked, and consistent in shape. Oversized, soft, or fragmented organoids created a variety of problems during culture and analysis and were thus discarded before the experiment started. Six organoids were selected at random on days 1, 3, 5, 7, 9, 11, and 13, and moved to a sterile Corning Falcon non tissue culture treated 48-well plate (Fischer Scientific) for analysis. These organoids had their media aspirated and replaced with 100 µL of room temperature media and 100 µL of room temperature Cell Titer Glo 3D ATP assay solution (Promega, Madison, Wis.). The plate was then shaken on a vortex (Fischer Scientific) at low speed for 10 minutes, and then allowed to rest at room temperature for an additional 20 minutes. 150 µL of the solution was then transferred to a white opaque 96-well plate and luminescence was quantified on a Varioskan Lux multimode microplate reader (Thermo Fisher, Waltham, Mass.). Each organoid was then weighed using a Mettler-Toledo microbalance (Mettler-Toledo, Columbus, Ohio). The recorded ATP signal was then divided by the organoid mass to normalize the signal to account for any remaining variance in organoid size.

Drug Study

Organoids were prepared as previously described and maintained in culture for 7 days. At this point, the media was swapped for fresh media containing acetaminophen (APAP, Sigma-Aldrich) at 100 µM, 1 mM, and 10 mM; and troglitazone (TRO, Sigma-Aldrich) at 10 µM, 100 µM and 1 mM. The drug-containing media was prepared by first dissolving the drug in DMSO (Sigma-Aldrich), and then preparing serial dilutions to produce the lower concentrations. The maximum DMSO concentration was 1% v/v, and so a control was added which was media supplemented with 1% DMSO. Another control, which was media with no supplement, was also employed in tandem. Each condition was performed in triplicate. The organoids were cultured for 2 days with their respective conditions, after which the organoids were subjected to the same ATP assay described previously, and mass normalized.

Immunohistochemistry

Organoids at day 1, 7, and 13, of the growth study were collected and prepared for IHC using three organoids per time point. The organoids were removed from culture, washed with DPBS, and then placed in 4% formaldehyde (PFA), prepared from a 32% stock solution purchased (Sigma-Aldrich), and gently shaken overnight at 4° C. The organoids were then removed from the PFA solution and placed in a 70% ethanol solution, made from 100% stock solution (Warner-Graham, Cockeysville, Md.), and left at 4° C. for storage. The organoids were removed from ethanol and embedded in paraffin. Sections of 4 µm thickness were cut from paraffin embedded HepG2 GNP bioink organoids with a microtome and placed on glass slides. The slides were deparaffinized in xylene, rehydrated, and washed three times in water. They were then permeabilized using 0.2% Triton-X100 in PBS, followed by three tris buffered saline (TBS, Sigma-Aldrich) washes, after which they underwent antigen retrieval. The slides were submerged in pH 6.0 AR Citrate buffer (PerkinElmer, Waltham, Mass.) in a bead bath at 95° C. for 20 minutes, washed three times with TBS, and then blocked using protein block (Dako, cat #X0909) for 10 minutes at room temperature. Organoids were stained using an Opal color kit (PerkinElmer, cat #NEL797001KT). Primary antibodies (Ki67, 1:100 dilution, abcam cat #ab16667) diluted in antibody diluent (Dako, Agilent, Santa Clara, Calif., cat #S3022) were applied over the course of 2 consecutive days overnight at 4° C. following each with an accompanying HRP 2o (anti-rabbit) for 30 minutes at room temperature, and then Opal fluorophore 570 & 540 diluted in amplification diluent at room temperature for 10 min. Slides were then washed three times with TBS supplemented with 0.5% TWEEN 20 (Sigma-Aldrich), and then stained with DAPI (1:10,000 dilution in PBS), followed by three TBS washes, mounted with Prolong glass (Invitrogen, Calsbad, Calif., cat #P36984), cover slipped, and imaged using an Olympus BX63 microscope (Olympus, Center Valley, Pa.).

Results and Discussion

Nanoparticle Analysis

The nanoparticles produced were roughly 300 nm in diameter immediately after synthesis as estimated from SEM micrographs. This was corroborated by the DLS analysis, showing that immediately following synthesis, the GNPs are roughly 400 nm in diameter, very similar to the estimation from the SEM micrograph. This is likely due to swelling from being immersed in water. These GNPs are also moderately stable in aqueous suspension with a $\zeta°$ of nearly +20 mV. This stability is necessary for the GNPs to remain in a homogeneous suspension in the bioink.

The purification and cryomilling processes needed to produce a powder that is able to be easily incorporated into the bioink has some effect on GNP morphology. During the purification process, the GNPs aggregate and fall out of solution. Specifically, the synthesis solution before and after neutralization, which causes large aggregates to form. This aggregation creates physically entangled GNPs that are unable to be mechanically separated. The cryomilling procedure dramatically reduces the size of the collected mass to aggregates that are 5 μm in diameter. This DLS analysis was corroborated by light microscopy between the two powders. The morphology of the individual GNPs has not changed, though they are introduced into the bioink now in aggregate form rather than as individual nanoparticles. These aggregates slowly break apart once redispersed into the bioink which will be shown later in the IHC analysis of the organoids. Once redispersed, the new $\zeta°$ is −20 mV, again indicating that moderate aqueous stability is achieved.

It may not be critical that individual GNPs are present in the bioink to induce the proper mechanics. As long as the particles are small enough to have significant physical interactions, like capillary action pulling two nearby particles together, as well as significant intermolecular interactions, like collagen fibers intermolecularly bonding to the GNP surfaces, then a mechanically stable bioink should still be produced.

Bioink Mechanics

Figure 7:
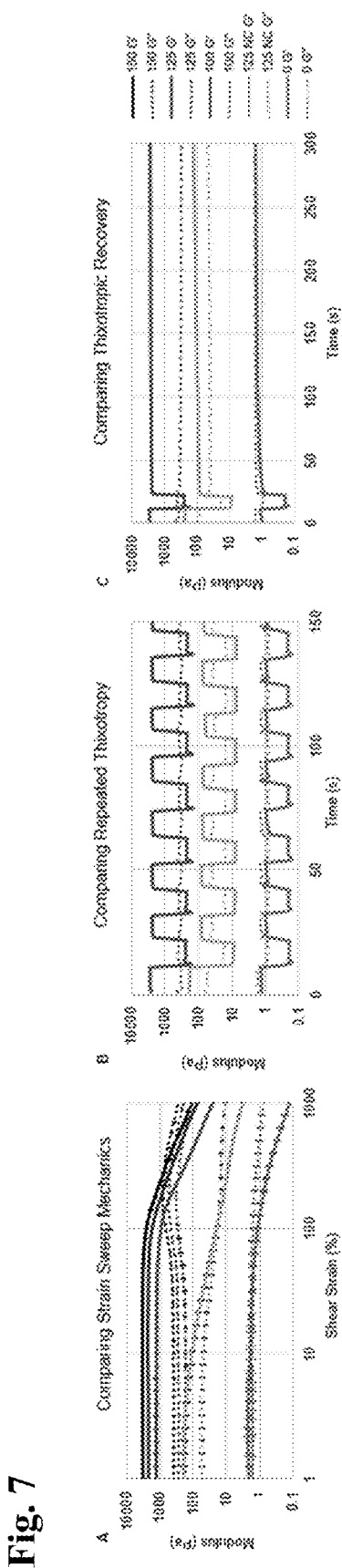
FIG. 7 shows graphs of rheological profiles of a bioink according to embodiments of the present invention. A) Strain sweep of various bioinks, B) Multiple low/high shear events showing the reversible nature of the bioinks, C) One high shear event showing the recovery rate of the bioinks. Legend number refers to GNP concentration in mg/mL, NC denotes non-cryomilled GNPs, error bars are ±1 standard deviation.

Rheological analysis of the GNP bioink confirms that a robust, self-supporting, thixotropic bioink has been produced with the cryomilled GNPs. The rheological profiles of the bioink with various amounts of cryomilled GNPs is shown in FIG. 7, panel A, along with the base bioink's mechanics for comparison. The GNP bioink profiles can be broken up into three different regimes: solid, transition, and liquid. The solid regime is present at low strains, typically below 50% shear strain. This is where the bioink behaves as a solid with a plateau in mechanics due to the physical and molecular interactions provided by GNPs. In this regime, the shear elastic modulus, G', is typically greater numerically than the shear loss modulus, G". The transition regime is present during moderate shearing, generally from 50% to 200% shear strain. During this period, the bioink's internal physical and molecular interaction begin to break down and the bioink transitions into a liquid. In this regime, the magnitudes of G' and G" converge. The liquid regime is present at high strain, typically greater than 200% shear strain, where G" is greater than G'. The strain at which the material transitions from a solid to a liquid is the thixotropic point. All of these regimes' shear strain values will shift up or down if more or fewer GNPs are present in the bioink because the amount of internal interactions present will also be going up or down proportionally. Here, the transition strains are 230%, 300%, and 350% for the 100 mg/mL, 125 mg/mL, and 150 mg/mL bioinks, respectively. From this collected data and printing experiments (discussed below), the 125 mg/mL bioink was selected as the standard bioink and was used in all subsequent experiments.

This transition from solid to liquid behavior based on the amount of shear present in the biomaterial is a critical feature for bioprinting. The initial solid regime proves that under normal resting conditions, the bioink will be able to withstand a load applied to it, meaning that it will not deform under its own weight or extra weight applied from above. This makes it a robust bioink that can be used to create hollow structures without any sacrificial support materials, such as pluronic F127 or cellulose nanofibers. The transition to a liquid due to high shear is needed for the bioink to be extrudable and to protect the cells. A very solid material would not extrude well and would require exceedingly high stresses to extrude. These high stresses could potentially rupture cells encapsulated within. This transition also allows for the bioink to flow under the high strain conditions, relieving internal stresses encountered within a bioprinter's nozzle, and then quickly transitioning back to a solid once deposited. This reversible strain dependent behavior can be seen in FIG. 7, panels B and C. FIG. 7, panel B shows how the bioink can cycle between low and high strain, and consequently cycle between solid and liquid, repeatedly without a significant loss in overall mechanics. The test itself is destructive, and so the bioink does not immediately fully recover its original mechanics during the low strain period before the next high strain period. FIG. 7, panel C shows that over several minutes time the bioink will recover to its initial mechanics. Extrapolating this linear recovery in G', it is estimated that the bioink will take approximately seven minutes to fully recover its solid regime mechanics.

The GNPs were not fully dispersed, and following the mechanical analysis of the bioink it is confirmed that full dispersion is not needed for the GNPs to induce the targeted mechanics. However, to achieve these mechanics, the aggregates must be of small enough size where those interactions becomes significant forces. Comparing the cryomilled GNP aggregates, which are 5 μm in diameter, to the non-cryomilled GNP aggregates, which are about an order of magnitude larger with varying sizes, the non-cryomilled aggregates do not achieve the proper mechanics. FIG. 7 also shows the rheological and thixotropic profiles of the GNP bioink made with non-cryomilled GNPs. The cryomilled particles are the right size to physically and intermolecularly interacting with each other and the dissolved biomaterials. The non-cryomilled particles are too large for those interactions to have a significant effect on mechanical behavior, and thus do not produce as robust of a material.

The physical interactions come in two forms: particle-particle and particle-fiber. The particle-particle interactions occur when two GNPs, or GNP aggregates, come close enough together in the hydrogel carrier solution such that capillary action is induced. This type of particle-particle interaction is also seen in sand castles, where the water shells surround the grains of sand interact with each other and the capillary action between those particles holds them together. The particle-fiber interactions come from the GNP aggregates interacting with the collagen fibers. These fibers will form spontaneously when the collagen is at a neutral pH and around room temperature. These soft fibers will entangle the GNP aggregates to create a network of solid particles held together in a web of collagen. The intermolecular interactions come from the individual molecular chains of collagen and hyaluronic acid interacting with the GNPs and aggregates. There are hydrophilic and hydrophobic sections of the GNPs and collagen chains that will self-assemble, as well as Van der Waals forces and hydrogen bonding between the GNPs, collagen, and hyaluronic acid. These intermolecular forces will the dominant force on the individual GNPs while the physical interactions will be dominant on the micron sized GNP aggregates due to their greater size.

Bioink Printing

From a quantitative standpoint, the mechanical analysis determined that the bioink should switch to a liquid regime when being forced through the printing nozzle, and quickly regain its solid regime mechanics post extrusion, making it a much improved printing material. The qualitative analysis of printing a model confirmed this prediction as well. The structure (similar to the structure shown in FIG. 6) was chosen to model intersecting vessels, something that modern bioprinters cannot produce without support materials or non-biological materials.

This print was performed at room temperature without any support material and the completed hollow structures remained free standing, with only some malformations due to heterogeneity within the bioink. Using a syringe pump print head that is controlled volumetrically, rather than a pneumatic print head, compensates for most of the heterogeneities of the bioink. However, when thicker regions of the bioink would pass through the nozzle, the printhead piece that connects to the syringe plunger deflects under the high load needed to extrude the material. This deflection causes potential energy to build up, like a spring, which is then released once the thicker portion of the bioink is through the nozzle, causing the print head to extrude more material than the target extrusion rate intends to extrude. These issues produced prints that were close to the original CAD model, with many areas being thicker than modeled due to over-extrusion. For comparison, the CAD model wall thickness was 0.5 mm while the printed model wall thickness averaged about 2 mm Even with these issues, this novel bioink is printable, and can withstand several layers built up without falling in on itself, eliminating the need for any additional support materials. Furthermore, this printing procedure is reproducible, creating very similar constructs in quick succession. Precision could be improved by improving the stiffness of the syringe pump hardware by fabricating it with more robust materials. This will decrease any deflection and improve extrusion consistency. Removing all air bubbles and heterogeneities from the material would also reduce the ability for potential energy buildup, though this is difficult since the material is thick and requires vigorous mixing.

Once UV crosslinked following printing, the completed structures are strong enough to be removed from the print surface and manipulated by hand. These structures remain intact once submerged with only minimal swelling. Swelling studies indicate that this bioink swells, on average, 25±5% m/m and 3.0±5% l/l. The models were submerged in DPBS to approximate the swelling that would be seen during culture conditions. The swelling caused some areas along the bottom of the prints to rupture. This part of the print is the thinnest section since layer heights are typically smaller for the first layers and because the bioink is just beginning to extrude during this time. This can be mitigated by including a raft or nozzle priming in the slicing software. The raft would increase the thickness of model bottom, and the nozzle priming would ensure that the material is ready to flow out of the nozzle immediately following pump start up. This was the only region of the prints that showed any signs of damage. This proves that the large quantity of GNPs does not affect UV crosslinking, and that prints are reproducible and will remain solid during culture.

Biocompatibility

Figure 8:
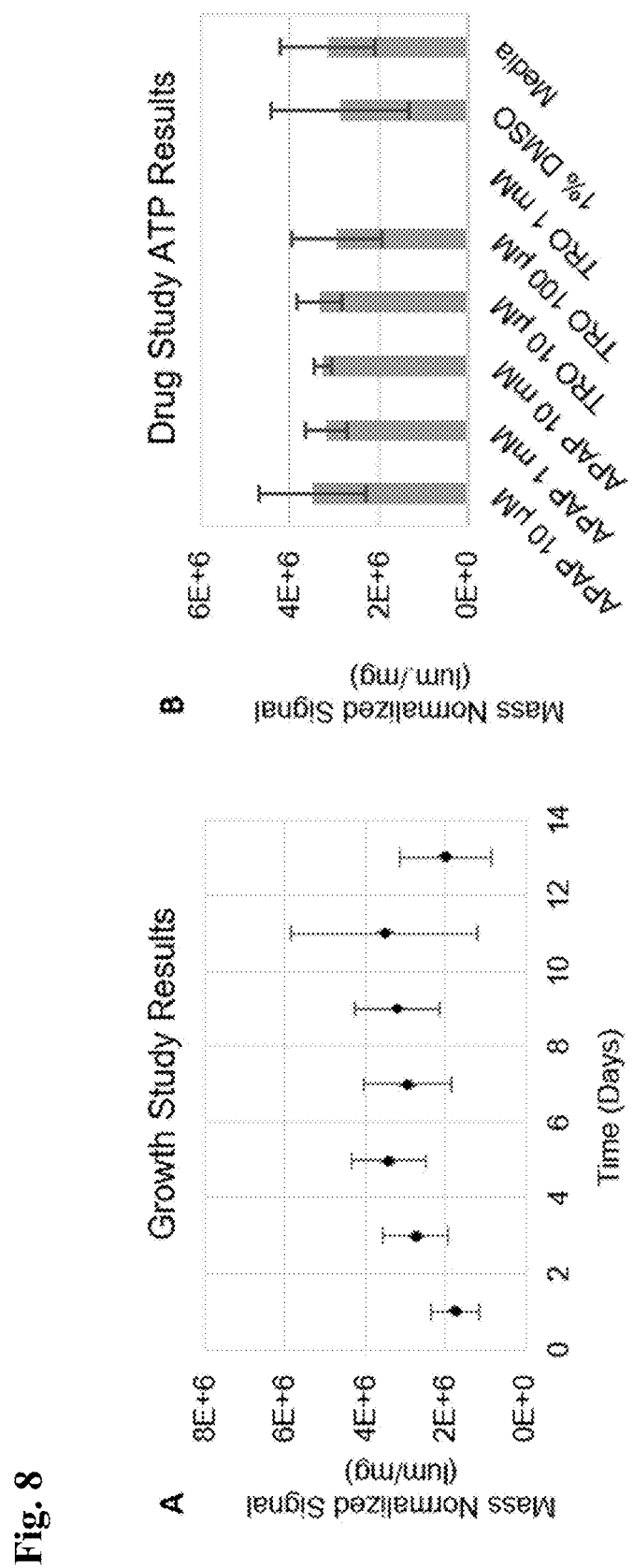
FIG. 8 shows results from a proliferation study. A) Mass normalized ATP signal of organoids made with the GNP bioink and 5 M/mL HepG2 cells cultured 1-13 days, with a reading every other day. n=6 per time point. B) Mass normalized ATP signal of organoids made with the GNP bioink and 5 M/mL HepG2 cells cultured for 7 days, then 2 days with media supplemented with the labeled drug, and then analyzed.

Results from the proliferation study confirm that this new bioink is capable of supporting HepG2 cells and their proliferation (FIG. 8). An increase in ATP signal is initially seen, corresponding to cell proliferation, and then a plateau occurs with increased variance. Comparing these results to the IHC results, this increase in variance comes from the directional proliferation and death of the cells. Large amounts of cells were seen at the surface of the organoid at day 13, compared to the original dispersion of the cells seen at day 1. This can be attributed to the size of the organoids, about 20 µL which will be discussed later, and poor diffusion through this bioink. This new bioink is very thick, which means that diffusion is going to be slower than typical bioinks and the maximum effective diffusion length is going to be shorter. Thus, as the organoid matures, the cells at the center of the bioprinted structure may be subject to necrosis because they are being starved of nutrients and can not remove their waste, while the cells at the edge will proliferate and expand. This flux of cell proliferation outwards and death inwards is the most likely cause of the variance at later time points. The IHC results corroborate the proliferation study's results with increased KI67 and DAPI signal at the outer rim of the organoids.

If the growth was continued past the two-week study, it is projected to stabilize at some ATP value where the entire outer shell of the organoid is filled with cells. The signal could increase if the cells were laying down their own ECM to create a larger organoid. Currently, this poor diffusion is a limitation of this new bioink. However, as bioprinting hardware advances and printing resolution increases, this may be solved by simply generating internal channels in all bioprinted structures. Alternatively, we are currently assessing ways to maintain the beneficial mechanical properties of this bioink, while decreasing GNP concentration, thus potentially increasing diffusion properties internally.

Another reason for the overall variance is due to the distribution of organoid sizes. The data presented in FIG. 8 was all normalized to the mass of each organoid before being averaged to compensate for organoid sizes. The pneumatic bioprinter used for organoid printing applies a constant pressure to the bioink. At constant pressure thin bioink portions extrude fast, producing large organoids, and thick bioink portions extrude slowly, producing smaller organoids. To mitigate that issue, the pressure was adjusted on the fly, between 150 kPa and 300 kPa, to produce more consistent organoids. This helped with the printing procedure but did not entirely fix the variability. Assuming that the cells were mixed homogeneously into the bioink, the smaller organoids would produce a smaller ATP signal compared to the larger organoids. This does not mean that the smaller organoids are less viable, but rather that there are fewer total numbers of cells present. Biocompatibility is an intrinsic property between the material and the cells, and so it does not depend on organoid size. To compensate for larger organoids producing a larger signal, without any increase in intrinsic biocompatibility, the signal was normalized to organoid mass. This improved the quantification, but is an admittedly tedious process that is not realistically scalable.

An improved method would be to normalize to the shell volume of the organoid, which is approximately equal to the surface area of the organoid times the max diffusion length of oxygen and nutrients in the media. This would be the viable volume of the organoid. If the signals were normalized to this value, then only variance in cell density would affect the ATP signal. However, this would have been much more difficult to do since the organoids were not perfect spheres, nor did they have smooth surfaces. The mass of each organoid was used as an approximation of this. Another way of decreasing variance is by using the syringe pump printhead to precisely control the extruded volume. Then, all organoids would be very nearly the same size and mass, negating the need for any normalization. Currently, software limitations prevent the use of the syringe pump printhead with this immersion printing method.

Aside from proliferation, the organoids also behaved as expected when challenged with different drugs. The right graph of FIG. 8 shows the results from the drug study. The APAP did not significantly harm the HepG2 cells, and the TRO reached a critical value between 100 µM and 1 mM where it became toxic. The acetaminophen was not expected to damage the HepG2 cells because this cell line does not metabolize acetaminophen at the same rate as other hepatic cell lines, preventing the buildup of the toxic metabolite. The troglitazone response was as expected with significant toxicity at 1 mM. Toxic effects are commonly reported above 100 µM.

The majority of current biologically-derived extrusion bioinks are not capable of creating self-supporting structures under ambient conditions without sacrificial support materials. However, the GNP-collagen-HA bioink described here is able to do just that. This bioink is comprised entirely of biological materials, all of which naturally occur within human tissue ECM. Successful harnessing of thixotropic mechanical properties enables this bioink to be mechanically stable and still be printable with high precision. As bioprinter hardware and software continue to improve, this bioink will also have improved precision and capabilities. We also demonstrate that this bioink is capable of supporting cell growth, as shown by a growth study with HepG2 cells. Incorporating GNPs loaded with growth factors or solubilized extra cellular matrix would further improve biocompatibility while retaining the robust mechanical properties. This bioink meets all the criteria of a successful extrusion bioink and will be employed in future more nuanced bioprinting efforts to create viable tissue constructs for therapeutic and diagnostic applications.

The foregoing is illustrative of the present invention, and is not to be construed as limiting thereof. The invention is defined by the following claims, with equivalents of the claims to be included therein.

That which is claimed is:

1. A composition comprising:
   gelatin nanoparticles having, on average, a diameter of about 150 nm to about 500 nm, wherein the gelatin nanoparticles are present in the composition in an amount of about 10 mg/mL to about 250 mg/mL;
   at least one polymer comprising thiolated hyaluronic acid and methacrylated collagen; and
   water,
   wherein the gelatin nanoparticles are glutaraldehyde crosslinked gelatin nanoparticles that are suspended in the composition,
   wherein the composition is thixotropic, and
   wherein the composition is extrudable through a 22 Gauge needle at room temperature and/or pressure.

2. The composition of claim 1, wherein the gelatin nanoparticles in the composition are in aggregates and the aggregates have, on average, a diameter of about 2 µm to about 8 µm.

3. The composition of claim 1, further comprising gelatin, that is not in the form of nanoparticles, in an amount of about 1 mg/mL to about 75 mg/mL.

4. The composition of claim 1, further comprising a thermal initiator or photoinitiator.

5. The composition of claim 1, further comprising live cells.

6. The composition of claim 1, wherein the composition has a pH of about 6.5 to about 5.

7. The composition of claim 1, wherein the composition is a hydrogel.

8. The composition of claim 1, wherein the composition is self-supporting.

9. The composition of claim 1, wherein the composition is liquid upon extrusion and after extrusion is solid.

10. The composition of claim 1, wherein the composition has an elastic modulus after extrusion and/or bioprinting that varies by less than about 20% compared to an elastic modulus of the composition prior to extrusion and/or bioprinting.

11. The composition of claim 1, wherein the composition, prior to and/or after deposition and/or subsequent optional crosslinking, has an elastic modulus from about 50 Pa to about 20,000 Pa.

12. The composition of claim 1, wherein the composition can be extruded with an applied mechanical stress in a range from about 1 kPa to about 80 kPa.

13. The composition of claim 1, wherein the composition has an elastic modulus G' and a loss modulus G" that are within ±20% or 10% of each other.

14. The composition of claim 1, wherein the composition has a stiffness of from about 0.05 kPa to 1 about 25 kiloPascal at room temperature and atmospheric pressure.

15. A method of making a three-dimensional construct, the method comprising:
    depositing the composition of claim 1 on to a substrate, thereby forming the three-dimensional construct.

* * * * *

UNITED STATES PATENT AND TRADEMARK OFFICE
CERTIFICATE OF CORRECTION

| | |
|---|---|
| PATENT NO. | : 11,213,608 B2 |
| APPLICATION NO. | : 16/533326 |
| DATED | : January 4, 2022 |
| INVENTOR(S) | : Skardal et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Seventh Day of February, 2023

Katherine Kelly Vidal
*Director of the United States Patent and Trademark Office*